United States Patent
Kindness et al.

(10) Patent No.: US 6,534,540 B2
(45) Date of Patent: Mar. 18, 2003

(54) COMBINATION AND METHOD OF TREATMENT OF CANCER UTILIZING A COX-2 INHIBITOR AND A 3-HYDROXY-3-METHYLGLUTARYL-COENZYME-A (HMG-COA) REDUCTASE INHIBITOR

(76) Inventors: George Kindness, 7207 Stonebrook Ct., Middletown, OH (US) 45044; Brooke Schumm, III, 2813 Thornbrook Rd., Ellicott City, MD (US) 21042; F. Timothy Guilford, 829 Forest Ave., Palo Alto, CA (US) 94301

( * ) Notice: Subject to any disclaimer, the term of this patent is extended or adjusted under 35 U.S.C. 154(b) by 4 days.

(21) Appl. No.: 09/912,703

(22) Filed: Jul. 25, 2001

(65) Prior Publication Data

US 2002/0086894 A1 Jul. 4, 2002

Related U.S. Application Data

(60) Provisional application No. 60/238,504, filed on Oct. 6, 2000, provisional application No. 60/245,592, filed on Nov. 17, 2000, provisional application No. 60/264,511, filed on Jan. 26, 2001, and provisional application No. 60/307,689, filed on Jul. 25, 2001.

(51) Int. Cl.$^7$ .............................................. A61K 31/34

(52) U.S. Cl. ........................................ 514/461; 574/473

(58) Field of Search ................................ 514/461, 473

(56) References Cited

U.S. PATENT DOCUMENTS

| | | |
|---|---|---|
| 4,231,938 A | 11/1980 | Monaghan |
| 4,346,227 A | 8/1982 | Terahara |
| 4,444,784 A | 4/1984 | Hoffman |
| 5,177,080 A | 1/1993 | Angerbauer |
| 5,273,995 A | 12/1993 | Roth |
| 5,354,772 A | 10/1994 | Kathawala |
| 5,747,459 A | 5/1998 | Rowe |
| 5,888,552 A | 3/1999 | Bounous |
| 6,136,804 A | 10/2000 | Nichtberger |
| 6,245,797 B1 | 6/2001 | Winokur |

FOREIGN PATENT DOCUMENTS

| | | |
|---|---|---|
| WO | WO 09641645 | 12/1996 |
| WO | WO 99/20110 | 4/1999 |
| WO | WO 00/031120 | 6/2000 |
| WO | WO 01/45698 | 6/2001 |

OTHER PUBLICATIONS

Shirama, T, Relation between Cyclooxygenase–2 Expression and Tumor Invasiveness and Patient Survival in Transitional Cell Carcinoma of the Urinary Bladder, Cancer vol. 92 (1): 188193 (Jul. 1, 2001) (Amer. Cancer Socy. 2001).

Evangelou, A, Is There any Role for Antioxidants in Cancer Prevention and Treatment, Abstract No. 85, IIAR Conference on Antioxidants in Cancer Prevention and Therapy, Jun. 4–7, 2001, Anticancer Research 21(3A): 1565 (May–Jun. 2001).

Galaris, D, Biological Antioxidants, Abstract No. 86, IIAR Conference on Antioxidants in Cancer Prevention and Therapy, Jun. 4–7, 2001, Anticancer Research 21(3A): 1565 (May–Jun. 2001).

Dovas A, The Role of Free Radicals and Metal Ions in the Generation and Prevention of Oxidative Disease, Abstract No. 84, IIAR Conference on Antioxidants in Cancer Prevention and Therapy, Jun. 4–7, 2001, Anticancer Research 21(3A): 1564–65 (May–Jun. 2001).

Robertson, F M et al, Cyclooxygenase as a Therapeutic Target in Breast Cancer, Abstract No. 176, IIAR Conference on Antioxidants in Cancer Prevention and Therapy, Jun. 4–7, 2001, Anticancer Research 21(3A): 1611 (May–Jun. 2001).

Clement IP et al, Methylselenocysteine Modulates Proliferation and Apoptosis Biomarkers in Premalignant Lesions of the Rat Mammary Gland, Anticancer Research 21: 863–868(2001).

Ratnasinghe D et al, Cyclooxygenase–2, P–glycoprotein–170 and Drug Resistance; Is Chemoprevention Against Multidrug Resistance Possible, Anticancer Research 21:2141–2148 (2001).

HSU, A et al, The Cyclooxygenase–2 Inhibitor Celecoxib Induces Apoptosis by Blocking Akt Activation in Human Prostate Cancer Cells Independently of Bcl–2, J. Biol. Chem. 275(15): 11397–11403, Apr. 14, 2000 (Amer. Socy. For Biochemistry and Molecular Biology, Inc. 2000).

Talley J et al, 4–[5–Methyl–3–phenylisoxazol–4–yl]–benzenesulfonamide, valdecoxib: a potent and selective inhibitor of COX–2, J. Medicinal Chemistry, 43(5): 775–777 (Mar. 9, 2000) (no text attached).

Talley J et al, N–[[5–methyl–3–phenylisoxazol–4–yl]phenyl]sulfonyl propanzmide, sodium salt, parecoxib solium: A potent and selective inhibitor of COX–2 for parenteral administration, J. Medicinal Chemistry, 43(9): 1661–1663 (May 4, 2000) (no text attached).

International Search Report with Date of Mailing of Mar. 25, 2002 for PCT/US01/31328 filed Oct. 6, 2001.

(List continued on next page.)

*Primary Examiner*—Raymond Henley, III
(74) *Attorney, Agent, or Firm*—Brooke Schumm, III; Daneker, McIntire, Schumm, Prince, Goldstein, Manning & Widmann, P.C.

(57) ABSTRACT

The inventors propose a combination of an HMG-CoA reductase inhibitor (also referred to as "HMG-CoA inhibitor (s)"), and COX-2 inhibitor for the treatment of cancer especially prostate cancer and a method of treatment of cancer by that combination, especially prostate cancer. The inventors propose a combination of an HMG-CoA reductase inhibitor, COX-2 inhibitor, and glutathione pathway enhancing and detoxifying compound, particularly cystine, for the treatment of cancer especially prostate cancer and a method of treatment of cancer by that combination, especially prostate cancer. Based on the clinical results of retardation, but not cure of cancer, the combination has the characteristic of sufficiently interfering with replication and apparently restoring the immune system capacity to manage cancer.

11 Claims, No Drawings

OTHER PUBLICATIONS

Bauer G. et al, Reactive Oxygen and Nitrogen Species: Efficient, Selective and Interactive Signals During Intercellular Induction of Apoptosis; Abteilung Virologie, Institute for Medizinische Mikrobiologie und Hygiene, Universität Freiburg, D–79104 Freiburg, Germany; *Anticancer Research* 20: 4115–4140 (2000).

Bolanos JP, Nitric Oxide, Mitochondrial Function and Excitotoxicity, Methods Findings Exp. Clin Pharmacol, 22(6): 375–77 (Prous Science 2000).

Wink D and Mitchell J, in "Chemical Biology of Nitric Oxide: Insights into Regulatory, Cytotoxic, and Cytoprotective Mechanisms of Nitric Oxide," Free Radical Biol. & Med. 25(4): 434–456, (Elsevier Sep. 1998).

Vogt A et al, "A Non–peptide Mimetic of Ras–CAAX: Selective inhibition of Farnesyl Transferase and Ras Processing," 270(2) J. Biological Chemistry 660–664 (Amer. Society for Biochemistry and Molecular Biology, Inc. Jan. 13, 1995).

Gunawardena K et al, "Vitamin E and Other Antioxidants Inhibit Human Prostate Cancer Cells Through Apoptosis," The Prostate 44:287–295 (Wiley–Liss, Inc. 2000).

Liu Xh et al, "Inhibition of Cyclooxygenase–2 suppresses Angiogenesis and the Growth of Prostate Cancer In Vivo," J. of Urology, 164:820–825 (Amer. Urological Ass'n Sep. 2000).

Abstract, Mohammed Si et al, "Expression of Cyclooxygenase–2 (COX–2) in Human Invasive Transitional Cell Carcinoma (TCC) of the Urinary Bladder," J. Urology 164:1844–45 (Amer. Urological Ass'n Nov. 2000).

Haddad J et al, "Thiol Regulation of Pro–Inflammatory Cytokines Reveals a Novel Immunopharmacological Potential of Glutathione in the Alveolar Epithelium" The Journal of Pharmacology and Experimental Therapeutics, vol. 296, No. 3, p. 996–1005 (Amer. Socy. For Pharm. And Experimental Therapeutics 2001).

Folkers, K et al, "Survival of Cancer Patients on Therapy with Coenzyme $Q_{10}$," Biochemical and Biophysical Research Communications; vol. 192, No. 1, 1993, Apr. 15, 1993, p. 241–245 (Academic Press 1993).

Cheng D et al, "Activation of Acyl–Coenzyme A: Cholesterol Acyltransferase by Cholesterol or by Oxysterol in a Cell–free System," *The Journal of Biological Chemistry*; vol. 270, No. 2, Issue of Jan. 13, pp. 685–695, (Am. Soc'y. for Biochem. and Molecular Biol. 1995).

Ly D et al, "Mitotic Misregulation and Human Aging," *Science*; Mar. 31, 2000; vol. 287, pp. 2486–2492 (Amer. Assoc for the Adv. Of Sci.).

Agarwal B et al, "Lovastatin Augments Sulindac–Induced Apoptosis in Colon Cancer Cells and Potentiates Chemopreventive Effects of Sulindac," *Gastroenterology* 1999; vol. 117:pp.838–847 (Amer. Gastroenterological Assoc.).

Thibault A et al, "Phase I Study of Lovastatin, and Inhibitor of the Mevalonate Pathway, In Patients with Cancer," *Clinical Cancer Research*; vol. 2, 483–491, Mar. 1996.

JI Yan–Shan, Xu Quing, Schmedtje, J, "Hypoxia Induces High–Mobility–Group Protein I(Y) and Transcription of the Cyuclooxygenase–2 Gene in Human Vascular Endothelium," Circulation Research 83(3):295–304, Aug. 10, 1998, (Amer. Heart Assoc. 1998).

Nelson D and Cox M, Lehninger Principles of Biochemistry, (Worth Publishers NY $3^{rd}$ ed. 2000) see especially pp. 528–542, 810–814, 840–843, 856–859, 1058–1063.

Salway J, Metabolism at a Glance, (Blackwell Science Oxford London 1999) pp. 12–15, 32–33, 48–51, 60–61, 68–69, 86–89.

Morini M, et al, "The role of the thiol N–acetylcysteine in the prevention of tumor invations and angiogenesis," Int'l J. of Biological Markers 14(4): 268–271 (Wichtig Editore 1999).

Rodan, G and Martin J, "Therapeutic Approaches to Bone Diseases," Science 289:1508–1514 (Sep. 1, 2000 Amer. Assoc for the Adv. of Sci.).

Ghosh J and Myers C, "Inhibition of arachidonate 5–lipoxygenase triggers massive apoptosis in human prostate cancer cells," Proc. Nat'l Acad. Sci. USA, 95:13182–13187 (Nat'l Acad. of Sci. Oct. 1998).

Salvucci, O., Carsana, M., Bersani, I., Tragni, G. and Janichini, A., "Antiapoptotic Role of Endogenous Nitric Oxide in Human Melanoma Cells," Cancer Research 61, 318, 326, Jan. 1, 2001, (Cancer Research 2001).

Suzuki, Y., Kondo, Y., Himeno, S., Nemoto, K., Akimoto, M., and Imura, N., "Role of Antioxidant Systems in Human Androgen–Independent Prostate Cancer Cells," The Prostate 43: 144–149 (2000 Wiley–Liss, Inc.).

Madaan, S., Abel, P.D., Hewitt, C.R., Stott, M.A., Stamp, G.W.H., and Lalani, E.N., "Cytoplasmic induction and over– expression of cyclooxygenase–2 in human prostate cancer: implications for prevention and treatment," BJU International (2000) 736–741 (2000 BJU International).

Silverstein, F., Faich, G., Goldstein, J., Simon L., Pincus, T., Whelton, A., Makuch, R., Eisen, G., Agrawal, N., Stenson W., Burr, A., Zhao, W., Kent, J., Lefkowith, J., Verburg, K., Geis, G., "Gastrointestinal Toxicity with Celecoxib vs Nonsteroidal Anti–inflammatory Drugs for Osteoarthritis and Rheumatoid Arthritis–13 The Class Study: A Randomized Controlled Trial," J. Amer. Med. Assoc., Sep. 13, 2000—vol. 284, No. 10, 1247–1255 (Amer. Med. Assoc. 2000).

Boireau, A., Budedat, P., Bordier, F., Coimbra, M., Meunier, M., Imperato, A., Moussaoui, S., "Effects of Ebselen, a Glutathione Peroxidase Mimic, in Several Models of Mitochondrial Dysfunction," Annals of NY Acad. Sci. 893: 254–257 (NY Acad. Of Sci. 2000).

Yasuda, H., "Prevention of Neurodegeneration by a Neuroprotective Radical Scavenger," Annals NY Acad Sci. 893: 430–433 (NY Acad. Of Sci. 2000).

Cohen, G., and Kesler, N., Monoamine Oxidase Inhibits Mitochondrial Respiration Annals NY Acad Sci. 893: 273–278 (NY Acad. Of Sci. 2000).

Lichtenstein, D. and Wolfe, M., "COX–2—Selective NSAIDs New and Improved?," (Editorial) J. Amer. Med. Assoc., Sep. 13, 2000—vol. 284, No. 10, 1297–1299 (Amer. Med. Assoc. 2000).

Kirschenbaum, A., Klausner, A., Lee, R., Unger, P., Yao, S., Liu, X. and Levine, A., "Expression of Cyclooxygenase–1 and Cyclooxygenase–2 in the Human Prostate," 2000, Elsevioer Science, In., p. 671–676, (Urology 56 (4) 2000).

Gupta, S., Srivastava, M., Ahmad, N., Bostwick, D., and Mukhtar, H., "Over–Expression of Cyclooxygenase–2 in Human Prostrate Adenocarcinoma," The Prostate 42:73–789 (2000), (2000 Wiley–Liss, Inc.).

Abstract—Carson, J., Kulik, G., and Weber, M., "Antiapoptotic Signaling in LNCaP Prostate Cancer Cells: A Survival Signaling Pathway Independent of Phosphatidylinositol 3'—Kinase and Akt/Protein Kinase B," The Prostate 42:79–80 (2000 Wiley–Liss Inc.).

Serhan, C., Clish, C., Brannon, J., Colgan, S., Chiang, N., and Gronert, K., "Novel Functional Sets of Lipid–derived Mediators with Antiinflammatory Actions Generated from Omega–3 Fatty Acids via Cyclooxygenase 2–Nonsteroidal Antiinflammatory Drugs and Transcellular Processing," J. Exp. Med. vol. 192, No. 8, Oct. 16, 2000 1197–1204 (The Rockefeller University Press New York).

Kulkarni, S., Jain N., and Singh, A., "Cyclooxygenase Isoenzymes and Newer Therapeutic Potential for Selective COX–2 Inhibitors," Methods Find Exp Clin Pharmacol 2000, 22(5): 291–298 (2000 Prous Science).

Kellogg, G., Crowell J., Steele, V., Lubet, R. Boone, CH. Malole W., Hawk, E., Lieberman, R., Lawrence, J., Kopelovich, L., Ali, I., Viner, J. and Sigman, C., "Progress in Cancer Chemoprevention", Annals of NY Acad. Sci., 889: 1–13, (NY Acad. of Sci. 2000).

Earnshaw, W., Martins, L. and Kaufmann, S., "Mammalian Caspases: Structure, Activation, Substrates, and Functions During Apoptosis," Annual Rev. Biochem 1999 68: 383–424 (Annual Reviews (1999).

Edwards, P. and Ericssaon, J., "Sterols and Isoprenoids: Signaling Molecules Derived From the Cholesterol Biosynthetic Pathway," Annu. Rev. Biochem. 1999, 68: 157–185 (Annual Reviews 1999) (pp. 157–175 attached).

Strittmatter, W. and Roses, A., "Apolipoprotein e and Alzheimer disease," Proc. Natl. Acad. Sci. USA, vol. 92, pp. 4725–4727, May 1995 (Nat'l Acad. Of Sci. 1995).

Oberley, T., Zhong, W., Szweda, and Oberley, L., "Localization of Antitoxidant Enzymes and Oxidative Damage Products in Normal and Malignant Prostate Epithelium," The Prostate 44: 144–155 (2000) (2000 Wiley–Liss, Inc.).

Denkert, C. Kobel, M., Berger, S., Siegert, A., Leclere, A., Trefzer, U. and Hauptmann, S., "Expression of Cyclooxygenase 2 in Human Malignant Melanoma," Cancer Research 61: 303–308, Jan. 1, 2001.

Chinery, R., Beauchamp, R., Shyr, Y., Kirland, S., Coffey, R. and Morrow, J., "Antioxidants Reduce Cyclooxygenase–2 Expression, Prostaglandin Production, and Proliferation in Colorectal Cancer Cells," Cancer Research 58: 2323–2327, Jun. 1, 1998.

Rao, G., Tate, M., Murthy, M., Hebbel, R., and White, J., "Influence of Antioxidants of Arachidonic Acid Metabolism and Platelet Function," Biochemical Medicine and Metabolic Biology 51: 74–79 (1994) (Academic Press, Inc.).

Sadkamoto, W., Fujie, K., Nishihira, J., Handa, H., Ueda, N., and Yamamoto, S., "Effect of vitamin E on expression of cyclooxygenase–2 in lipopolysaccharide–stimulated rat macrophanges," Biochimica et Biophysica Acta 1304 (1996) 139–144 (Elsevier Science B.V. 1996).

Paglin, S., Hollister, T., Delohery, T., Hackett, N., McMahill, M., Sphicas, E., Domingo, D., and Yahalom, J., "A Novel Response of Cancer Cells to Radiation Involves Autophagy and Formation of Acidic Vesicles," Cancer Research 61, 439–444, Jan. 15, 2001.

Josse, C., Legrand–Poels, S., Piret, B., Sluse, F., and Piette, J., "Impairment of the Mitochondrial Electron Chain Transport Prevents NF–kB Activation by Hydrogen Peroxide," Free Radical Biology & Medicine, vol. 25, No. 1, pp. 104–112 (Elsevier Science 1998).

Chen, K., Suh, J., Carr, A., Morrow, J., Zeind, J., and Frei, B., "Vitamin C suppresses oxidative lipid damage in vivo, even in the presence of iron overload," Am J Physical Endocrinol Metab 279: E1406–E1412, 2000 (The American Physiological Society 2000).

Coffey, R., Hawkey, C., Damstrup, L. Graves–Deal, R., Daniel, V., Dempsey, P., Chinery, R. Kirkland S., Dubois,R. Jetton, T. and Morrow, J., "Epidermal growth factor receptor activation induces nuclear targeting of cyclooxygenase–2, basolateral release of prostaglandins, and mitogenesis in polarizing colon cancer cells," Proc. Natl. Acad. Sci. USA Col. 94, pp. 657–662, Jan. 1997 (Nat'l Acad. of Sci.).

Moutet, M., D'Alessio, P., Malette, P., Devaux, V. and Chaudiere, J., "Glutathione Peroxidase Mimics Prevent TNFa–and Neutrophil–Induced Endothelial Alterations," Free Radical Biology & Medicine vol. 25, No. 3, pp. 270–280(Elsevier 1998).

Landino, L., Crews, B., Timmons, M., Morrow, J., and Marnett, L., "Peroxynitrite, the coupling product of nitric oxide and superoxide, activates prostaglandin biosynthesis," Proc. Natl. Acad. Sci. USA; vol. 93, pp. 15069–15074, Dec. 1996 (Nat'l Acad. of Science).

Zi X and Agarwal R, "Novel cancer chemopreventive effects of a flavonoid antioxidant silymarin: inhibition of mRNA expression of an endogenous tumor promoter TNF alpha," Biochem. Biophys. Res. Commun. 239(1):334–9 Oct. 9, 1997 (abstract Nat'l Lib. of Med. Pubmed PMID 9345320.

Valenzuela A and Garrido A, "Biochemical bases of the pharmacological action of the flavonoid silymarin and of its structural isomer silibinin," Biol Res. 27(2): 105–112 (1994) Abstract Nat'l Lib. of Med. Pubmed PMID: 8640239.

Fosslien E, "Biochemistry of Cyclooxygenase (COX)–2 Inhibitors and Molecular Pathology of CIX–2 Neoplasia," Crit. Rev. in Clin. Labor. Sci. 37(5):431–502 (CRC Press LLC 2000) [footnotes at pp. 487–502 omitted].

Chung L W K, Isaccs W and Simons, J (editors), "Prostate Cancer: Biology, genetics, and the New Therapeutics," ch. 21 by Brooks J and Nelson W, "Chemoprevention of Prostate Cancer," pp. 365–375 (Humana Press Totowa NJ 2001).

Sambongi Y et al, "Mechanical Rotation of the c Subunit Oligomer in ATP Synthase (F0/F1): Direct Observation," Science 286: 1722–1724, Nov. 26, 1999 (Nat'l Acad. of Sci. 1999).

Chauret et al, "In vitro metabolism considerations, including activity testing of metabolites, in the discovery and selection of the COX–2 inhibitor etoricoxib (MK–0663)" Bioorg. Med. Chem. Lett. 11(8): 1059–62, Apr. 23, 2001 (Abstract Nat'l Lib. of Med. Pubmed PMID 11327589).

Nat'l Cancer Institute, "Interleukin–12 in Treating Patients with Refractory Advanced–Stage Ovarian Cancer or Abdominal Cancer," Study recruiting patients from www.clinical trials.gov, NLM ID NCT00003439 Jan. 1, 2001 last update.

Nat'l Cancer Institute, "R115777 in Treating Patients with Progressive, Metastatic Prostate Cancer that has no responded to Hormone Therapy," Study recruiting patients from www.clinical trials.gov, NLM ID NCT00005848 Aug. 1, 2000 last update.

Hong Sh et al, "Relationship of arachidonic acid metabolizing enzyme expression in epithelial cancer cell lines to the growth effect of selective biochemical inhibitors," Cancer Research 59(9):2223–28, May 1, 1999 Abstract Nat'l Lib. of Med. pubmed PMID 10233261.

Tong M, "Induction of NAD (+) linked 15–hydroxyprostaglandin dehydrogenase expression by androgens in human prostate cancer cells," Biochem. Biophys. Res. Commun. 276(1): 77–81 (Sep. 16, 2000) Abstract Nat'l Lib. of Med. Pubmed PMID 11006085.

Masferrer JL et al, "Antiangiogenic and antitumor activities of cyclooxygenase-2 inhibitors," Cancer Research 60(5): 1306–11, Mar. 1, 2000 Abstract (Nat'l Lib. of Med. Pubmed PMID:10728691.

Nohl H et al, "Antioxidant–derived prooxidant formation from ubiquinol," Free Radical Biol. & Med. 25(6): 666–675 (Elsevier Science 1998).

Tsuchida S, Critical Reviews in Biochem. and Molecular Biol. 27(4,5): 337–384 (CRC Press Inc. 1992) (attached are pp. 337–338, 342–343, 355–365).

Heber, D et al, Cholesterol–lowering effects of a proprietary Chinese red–yeast–rice dietary supplement, Am. J. Clin. Nutr. 69(2): 231–Feb. 6, 1999. Abstract Nat'l Lib. of Med. Pubmed PMID 9989865.

Skottovana N et al, "Silymarin as a Potential Hypocholesterolaemic Drug," Physiol. Re. 47:1–7 (1998) (Inst. of Phys., Acad. Of Sci. Czech Republic, Prague 1997).

Demhlow C, "Scavenging of Reactive Oxygen Species and Inhibition of Arachidonic Acid Metabolism by Silibinin in Human Cells," Life Sciences 58(18): 1591–1600 (Elsevier Science Inc. 1996)pp. 1591–1599 attached.

Zhao J and Agarwal R, "Tissue distribution of silibinin, the major active constituent of silymarin, in mice and its association with enhancement of phase II enzymes: implications in cancer chemoprevention," Carcinogenesis 20(11):2101–2108 (Oxford University Press 1999).

Agarwal R et al., "Inhibitory effect of silymarin, an anti-hepatoxic flavonoid, on 12 O–tetradeconoylphorbol–13–acetate–induced epidermal ornithine decarboxylase activity and mRNA in SENCAR mice," Carcinogenesis 15(6):1099–1103 (Oxford University Press 1994).

Bhatia N et al, "Inhibition of human carcinoma cell growth and DNA synthesis by silibinin, an active constituent of mile thisle: comparison with silymarin," Cancer Letters 147 (1999): 77–84 (Elsevier Science Ireland Ltd. 1999).

Soslow et al, "COX–2 is expressed in human pulmonary, colonic, and mammary tumors," 89(12): 2637–2645 (Dec. 15, 2000) (American Cancer Socy. 2000).

Miller T et al, "5–HETE Congeners as Modulators of cell proliferation," Bioorg Med. Chem. Lett. 10(17):1913–16 (Sep. 4, 2000) abstract Nat'l Lib. of Med. Pubmed PMID 10987416.

Zhao J et al, "Significant inhibition by the flavonoid antioxidant silymarin against 12–O–tetradeconoylphorbol–13–acetate–caused modulation of antioxidant and inflammatory enzymes, and cyclooxygenase 2 and interleukin–1 alpha epression in Sencar mouse epidermis: implications in the prevention of stage I tumor promotion," Mol Carinog. 26(4):321–333, Dec. 1999 Abstract Nat'l Lib. of Med. Pubmed PMID 10569809.

Dehmlow C, et al, "Scavenging of reactive oxygen species and inhibition of arachidonic acid metabolism by silibinin in human cells," Life Science 58(18): 1591–1600 (1996) Abstract Nat'l Lib. of Med. Pubmed PMID 8649189.

Yergey JA et al, "In vitro metabolism of the COX–2 inhibitor DFU, including a novel glutathione adduct rearomatization," Drug Metab. Dispos. 29(5):638–44, May 2001 Abstract Nat'l Lib. of Med. Pubmed PMID 11302928.

Zi X, "A flavonoid antioxidant, silymarin, inhibits activation of erbB1 signaling and induces cyclin–dependent kinase inhibitors, G1 arrest, and anticarcinogenic effects in human prostate carcinoma DU145 cells," Cancer Research, 58(9):1920–29 May 1, 1998 (Abstract Nat'l Lib. Of Med. Pubmed PMID 9581834).

Abstract and Paper, Dhakshinamoorthy et al, "Antioxidant regulation of genes encoding enzymes that detoxify xenobiotics and carcinogens," $6^{th}$ Internet World Congress for Biomedical Sciences, www.uclm.es/inabis2000/symposia/ Jan. 24, 2000.

Manna SK et al, "Sillymarin suppresses TNF–induced activation of NF–kappa B, c–Jun N–terminal kinase, and apoptosis," J. Immunol 163(12):6800–09 (Dec. 15, 1999) Abstract Nat'l Lib. of Med. Pubmed PMID 10586080.

Rui YC, "Advances in pharmacological studies of silymarin," Mem. Inst. Oswaldo Cruz 1991:86 Sup. 2:79–85 Abstract Nat'l Lib. Of Med. Pubmed PMID 1842018.

Sparrow C et al, "Simvastatin has anti–flammatory and antiatherosclerotic activities independent of plasma cholesterol lowering," Arterioscler. Thromb. Vac. Biol. 21(1): 115–21 (Jan. 2001) Abstract Nat'l Lib. of Med. Pubmed PMID 11145942.

Paramentier M, et al, "Regulation of lipopolysaccharide–mediated interleukin–1 beta release by N–acetylcysteine in THP–1 cells," Eur. Respir. J. 16(5): 933–39, Nov. 2000 (Abstract Nat'l Lib. of Med. Pubmed PMID 11153595).

Hata S et al, "Synthesis of sterols and 5–lipooxygenase products are required for the G1–S phase transition of interleukin–2–dependent lymphocyte proliferation," Microbiol Immunol. 31(12): 1231–44 (1987) (Abstract Nat'l Lib. Of Med. Pubmed PMID 3131638).

Inoue I et al, "Lipophilic HMG–CoA reductase inhibitor has an anti–flammatory effect: reduction of MRNA levels for interleukin 1 beta, interleukin–6, cyclooxygenase–2, and p22phox by regulation of peroxisome proliferator–activated receptor alpha (PPARalpha) in primary endothelial cells," Life Sci. 67(8): 863–76 (Jul. 14, 2000) Abstract Nat'l Lib. of Med. Pubmed PMID 10946846.

Bounos G, Whey Protein Concentrate (WPC) and Glutathione Modulation in Cancer Treatment, Anticancer Research 20: 4785–4792 (2000).

COMBINATION AND METHOD OF TREATMENT OF CANCER UTILIZING A COX-2 INHIBITOR AND A 3-HYDROXY-3-METHYLGLUTARYL-COENZYME-A (HMG-COA) REDUCTASE INHIBITOR

CONTINUATION DATA

This invention claims the benefit of Provisional Applications No. 60/238,504 filed Oct. 6, 2000, No. 60/245,592 filed Nov. 17, 2000, No. 60/264,511 filed Jan. 26, 2001, and No. 60/307,689 filed Jul. 25, 2001, which provisional applications are incorporated by reference.

SUMMARY OF INVENTION

The inventors propose a combination of an HMG-CoA reductase inhibitor (also referred to as "HMG-CoA inhibitor (s)"), and COX-2 inhibitor for the treatment of cancer especially prostate cancer and a method of treatment of cancer by that combination, especially prostate cancer. The inventors propose a combination of an HMG-CoA reductase inhibitor, COX-2 inhibitor, and glutathione pathway enhancing and detoxifying compound, particularly cystine, for the treatment of cancer especially prostate cancer and a method of treatment of cancer by that combination, especially prostate cancer. Methods of manufacturing are also claimed. The invention, however, is applicable to cancers generally in mammals and the reference to human biochemistry is not intended to be limiting, but illustrative. The term patient or body or reference to humans is utilized for convenience, but includes all mammalian patients or bodies.

BACKGROUND

Traditional cancer treatments have generally used an approach which is focused on directly attacking cells with a propensity to divide. The cancer cell is viewed as a bad cell that must be eliminated. The methods and combinations chosen focus on destruction of the dividing cell, or chemical attack of the cell.

This invention proposes a different methodology. The first premise is to recognize the highly adaptable characteristics and durable biochemistry of the cancer cell from a biochemical and genetic viewpoint. Many cancer cells are body cells gone awry. The literature solidly suggests that cancer cells in a patient's body have a capability to readapt their functions to adjust to ambient conditions. A patient's body also has an impressive capability to adapt to changing macro-environmental conditions, as well as the micro-environmental conditions in biological chemistry internal to the cell.

Cancer cells, in a genetic or evolutionary sense, are not "bad" cells. Rather, they are efficient cells; in fact, they are highly efficient cells in a certain way. They use relatively less oxygen for the total amount of activity they undertake, and they divide rapidly, enabling them by normal processes of mutation and evolution to adapt their genetic material more quickly. Were the systems and cells in the rest of our bodies equally efficient, we would be greater evolutionary giants than we stand today.

For any attack on cancer cells to be successful, unless they can be physically cut out of the body by surgery, the attack cannot be "too successful." Cancer cells are us, and in a much slower evolutionary way, we are cancer cells. Too much success in damaging cancer cells pharmacologically in the prior art has often been destructive of the host body.

Returning to and illustrating the principle that the body is one large biochemical machine, suppose drops of salt water with colored salt are added to a larger volume of pure water in a container. The body is close to 98% seawater, meaning traditional $H_2O$ water with many other substances and compounds floating in the water. At first the drops would appear whole, but gradually the drops would dissipate so that the entire container might take on a tinge of color. The salt would be dispersed throughout the container so that, once equilibrium was established, all parts of the container had an equal concentration of the salt for each small volume of water. Before that equilibrium was established, the drops of colored water carrying the salt would tend to flow from areas of higher concentration (such as the original drops) to areas of lower concentration in the container (such as the "corners" of the container where there was originally no colored water. That tendency to flow from areas of greater concentration to lesser concentration calls for a resolution of osmotic imbalance generating a pressure gradient and is very important to understanding this invention.

Our bodies are not however, a mere blob of water without structure. Cells are a packet of "sea water" with many compounds in the water surrounded by a membrane. Just like a pile of wet sand full of water will not hold its shape for building a sand castle, but is very strong and can form a formidable dike if the wet sand is in a bag, the contents of cells in a body, surrounded by a membrane, give the body of humans its structure. Metaphorically, human beings are a standing milieu of tiny piles of sea water in bags called membranes.

On a microscopic scale, the body acts the same way as the earlier described container of salt water. Drops in the form of minute or low concentrations of biologically significant chemicals gradually diffuse throughout our body through links from the membrane bags of sea water in systems of pipes called blood and lymph vessels. Taking advantage of differences in concentration, the blood vessels biochemically "transport" substances either to cells or from cells. Within cells, biochemicals travel by osmosis affected and influenced by biochemical cycles. When cells are short of glucose, the basic fuel product of food, cells have a lower concentration of a substance they need, and if there is a higher concentration of glucose in an adjacent capillary which has a blood cell, some of that glucose flows across the membrane in a complicated biochemical transport mechanism to restore the concentration of glucose in the cell, naturally depleting the concentration in the blood stream.

To complicate the picture in the body context, not all membranes allow all substances to pass. Some are only semi-permeable, allowing only compounds in certain shapes or sizes to pass. For those semi-permeable membranes, if the concentration of compounds on one side of the membrane changes, for instance, increases, then water will flow to that side of the membrane to re-balance the concentration.

Relying on the premise that cancer cells need to divide or replicate (since if they are stable they either pose less danger or are gradually eliminated), the invention takes advantage of that tendency of cancer cell's needs which cause chemicals to flow from areas of greater concentration to those of lesser concentration. First, cancer cells need energy in order to do what they do the most and best, which is to divide or replicate. Energy in a cell is provided by the Krebs cycle. Cancer cells, because they divide frequently, are very sensitive to interference with their energy processes.

Second, when any cell divides, including cancer cells, the bag around the cell which is the membrane has to split into two bags. This presents two problems for the cancer cell. One, the cancer cell needs relatively more cholesterol in order to replicate successfully than a normal cell needs for its normal activities. Two, the membrane is necessarily weakened somewhat as the dividing process occurs and the cell transforms from one cell into two cells like a sandwich being pulled apart into two halves.

The human body is not completely helpless against cancers. However, cancer cells are relatively good at deceiving or confusing the immune system of our body into believing that the cancer cells are not as bad as they really are, or alternatively, because of rapid replication and evolution, developing defenses against the immune system. Further, as cancer progresses, it damages the body's immune system, including by triggering long-term inflammatory mechanisms.

In total, this invention proposes to use a novel combination to inhibit key biochemical cycles in a way that causes more damage to the cancer cell than to other cells, to decrease long-term inflammation, and to improve and sustain the body's immune system so it can better attack the weakened cancer cells and support the body's remaining essential functions. The inventors propose to selectively modify several biochemical pathways so as not to destroy overall body function, but disproportionately harm cancer cells, to enhance the body's immune system in order that the immune system may attack the cancer cells, and by stressing the cancer cell, to inhibit the cancer cell's normal resistance to immune system function, and to protect the body's normal cells.

The inventors propose a method of treatment of cancer, particularly prostate cancer and pancreatic cancer, by a particular combination of drugs for that purpose which has not been previously proposed for that purpose. The inventors propose a method of treatment of cancer involving a novel combination of drugs which simultaneously slows the cancer but also enables the body's immune system to better attack or fend off the cancer.

The first object of this invention proposes to selectively interfere with the production of cholesterol in two places in a way that impairs the energy cycle of all cells but which normal cells can overcome because they need less energy to survive because they are not dividing, but in a way that has a disproportionate and damaging effect on cancer cells which must replicate, or the cancer will not spread. This object takes advantage of the cancer cell's requirement for cholesterol causing biochemical signaling for cholesterol if not adequate to meet the replicating cancer cell's needs.

A second object is to selectively modify a biochemical cycle that targets inflammatory mechanisms in the body. One of the most damaging aspects of cancer cells is that they trigger an extended inflammatory response in the body. Further, as cancer progresses, it damages the body's immune system by a number of mechanisms, including the triggering of an extended inflammatory response in the body, which is less efficient in the removal of cancers. Prostaglandins are some of the most important signals to cause inflammatory responses. The biochemical cycle that we propose to selectively inhibit is an important cycle that converts arachidonic acid to several forms of prostaglandins. That cycle is the cyclooxygenase or COX cycle.

Biochemical cycles have many intermediate steps in them and the intermediate compounds are known as "intermediates." One of those intermediates in the cyclooxygenase cycle is prostaglandin H2 synthase, which has two forms: COX-1 and COX-2. COX-1 is known as a housekeeping substance which helps generate substances that protect the stomach. Ding et al, "Blockade of Cyclooxygenase-2 Inhibits Proliferation and Induces Apoptosis in Human Pancreatic Cancer Cells, vol. 20 AntiCancer Research, 2625–2632 (2000). Aspirin inhibits COX-1 and therefore, because it inhibits a substance that protects the stomach, often has gastrointestinal side effects. Recently, substances have become available that selectively inhibit COX-2 enzymes over COX-1 enzymes. COX-2 enzymes regulate pain, inflammation and fever, i.e. inflammatory mechanisms.

The COX-2 inhibitors in this invention interfere with the transformation of a substance called squalene to cholesterol. There are numerous intermediates from squalene to cholesterol.

Earlier in the biochemical cycle that produces cholesterol is a substance called Acetyl-CoA enzyme. It is converted to an intermediate called mevalonate by an enzyme called 3-hydroxy-3-methylglutamate-CoA reductase ("HMG-CoA"). Recent pharmaceutical advances have produced a number of substances that inhibit the activity of HMG-CoA and slow the production of cholesterol. HMG-CoA inhibitors have been used and are claimed to be used to reduce cholesterol to slow various blood vessel and related heart disease problems which we generally refer to as cardiovascular disease.

A third object of this invention is to utilize the more optimal function of cystine in the pH balance of a normal cell than in the lower pH of a cancer cell. The administration of cystine, enhances the body's immune system benefitting the total body disproportionately to any benefit cystine administration may have for a cancer cell.

In sum, the premise of this invention is that the cancer cells divide rapidly, that they have significant anaerobic glycolytic processes, and that the body is one large biochemical machine in which we can play to the strength of our body to the detriment of the cancer cell.

The science behind the combination is based on a triad of attacks on the biochemical pathways contributing to cancer cell replication.

Cancer cells must necessarily replicate for a "cancer" to thrive. Attacks on biochemical cycles at points where replication are involved are a favored approach. Cancer cells are particularly vulnerable to interference with lipid cell membrane status and ATP synthesis.

The COX-2 inhibitor interferes with the operation of the cyclooxygenase cycle from which are generated prostaglandins critical in cell division chemistry, and inhibits the "long-term" effects of inflammatory effects. Fosslien, "Biochemistry of Cyclooxygenase (COX)-2 Inhibitors and Molecular Pathology of COX-2 in Neoplasia," Crit. Rev. in Clin. Lab. Sci. 37(5): 431–502 (November 2000).

Tumors and their malignant cancer cells multiply in an exponential growth pattern relative to other body cells. Any retardation of replication will have an exponential effect in slowing cancer growth. Any apoptosis of a cancer cell has a disproportionately exponential effect in retarding cancer. Current treatments such as chemotherapy and radiation therapy which have severe quality of life effects have relied on this disproportionately exponential effect to achieve what benefits those treatments do achieve for extending the life of patients.

This invention has the further benefit as distinct from prior art of accomplishing its benefits with substantially less interference with quality of life than chemotherapy and radiation therapy(ies) in particular.

Discussion of Certain Specific Patent and Literature Art

One patent, Winokur, PCT Appl. US98/21901, filed Oct. 16, 1998, published as WO99/20110 entitled "Combination Therapy for Reducing the Risks Associated with Cardio and Cerebrovascular Disease", and a corresponding U.S. Pat. No. 6,245,797, claims a combination of a COX-2 inhibitor with an HMG-CoA inhibitor for treating, preventing, and/or reducing the risk of atherosclerosis and atherosclerotic disease events and a method of using a COX-2 inhibitor with an HMG-CoA inhibitor for treating, preventing, and/or reducing the risk of atherosclerosis and atherosclerotic disease events. Another patent, Nichtberger, U.S. Pat. No. 6,136,804, Oct. 24, 2000, entitled "Combination therapy for treating, preventing, or reducing the risks associated with acute coronary ischemic syndrome and related conditions" proposes the utilization for an antiplatelet agent in combination with a therapeutically effective amount of a COX-2 inhibitor to treat, prevent or reduce the risk of acute coronary ischemic syndrome, thrombosis, and related vascular problems.

Certain other literature has suggested that COX-2 inhibitors may have efficacy toward certain cancers. A review article sets out a good summary of COX-2 inhibitors. Fosslien "Biochemistry of Cyclooxygenase (COX)-2 Inhibitors and Molecular Pathology of COX-2 in Neoplasia," Crit. Rev. in Clin. Lab. Sci. 37(5): 431–502 (2000). In unrelated research, COX-2 inhibitors were reported to be inhibiting certain cancers, particularly familial adenomatous polyposis. See, 319 (7218) British Medical Journal 1155 (Oct. 30, 1999). COX-2 inhibitors, in that instance, celecoxib, a COX-2 inhibitor manufactured by G. D. Searle, and sold under the brand name Celebrex, had caused a reduction in adenomatous polyps which are a virtual guarantor of cancer of the colon if left untreated. Cyclooxygenase-2 had been implicated in colorectal cancer and colonic tumorigenesis. See, "The Relationship Between Cyclooxygenase-2 Expressions and Colorectal Cancer", 282(13) J. Amer. Med. Ass'n:1254–1257 (Oct. 6, 1999).

Both celecoxib and rofecoxib are suggested to have similar effects. See, Vol. 56(2) Amer. J. of Health-System Pharmacy: 106–107 (Jan. 15, 1999). Unfortunately, like many (nonsteroidal anti-inflammatory drugs (NSAIDs), the COX-2 inhibitors are felt to cause a range of gastrointestinal problems.

Based on the pharmaceutical product description of Merck for simvastatin, which description is adopted herein and attached for reference, and which drug is marketed as ZOCOR, a registered trademark of Merck, simvastatin functions in a similar way to lovastatin, another drug marketed by Merck under the registered trademark of MEVACOR, the pharmaceutical product description for which is adopted herein and attached for reference. Both are derived from *aspergillus terreus.*

Certain literature has suggested that HMG-CoA inhibitors may have efficacy toward certain cancers. Based on an article entitled, "Caspase-7 is Activated During Lovastatin Induced Apoptosis of the Prostate Cancer Cell Line LNCaP" 58(1) Cancer Research: 76–83 (1998), and a second article "Inhibition of the 3-hydroxy-3methylglutaryl-coenzyme A reductase pathway Induces p53-independent Transcriptional Regulation of p21(WAF1/CIP1) in human prostate carcinoma cells", 273(17) J. Biol. Chem.: 10628–23, (1998), lovastatin had therapeutic value in treating prostate cancer. Patients to whom were administered lipid lowering/modifying drugs such as lovastatin were suggested to be more cancer-free than those using bile acid-binding resins. See, 3-Hydroxy-3-Methylglutaryl Coenzyme A Reductase Inhibitors and the Risk of Cancer: A Nested Case-Control Study, 160(5) Archives of Internal Med: 2363–2368 (2000). "Therapeutic Approaches to Bone Diseases [Bone Remodeling and Repair: Review]," Science, 289(5484), Sep. 1, 2000:1508–1514.

No patent or literature suggests that the substances be combined to treat cancer nor is the synergistic effect set forth in this specification suggested or described.

No patent or literature suggests the preferred embodiment that a COX-2 inhibitor be combined with an HMG-CoA inhibitor to retard cancer and be further combined with a glutathione-cycle enhancing compound such as cystine, cysteine, or N-acetyl-cysteine, also called NAC, to improve immune system competency to further retard cancer.

No literature suggests another preferred embodiment: using a COX-2 inhibitor and HMG-CoA inhibitor set forth in this invention to retard cancer.

Reduction to Practice

The combination of a selective COX-2 inhibitor and an HMG-CoA reductase inhibitor exhibits the unexpected property of enabling management of cancer. This has been demonstrated in two specific instances. Both patients were diagnosed with Stage 4 metastatic cancer and were refractory to other treatments. The first patient had prostate cancer and showed a PSA (prostate specific antigen-a widely accepted marker of prostate cancer activity) of 71 according to the patient. The patient was placed on a regimen of VIOXX and MEVACOR, and has survived with good quality of life such as mowing his lawn, steady weight, and the like while the patient's PSA fell from tests conducted by one of the inventors to less than 2.5 with scan-documented lack of progression. A second patient diagnosed with pancreatic cancer which was also refractory to other treatment was placed on a regimen of VIOXX and MEVACOR with a whey supplement containing cystine and has survived over two months and gained some weight since first presenting while sustaining a reasonable quality of life. Pancreatic cancer is one of the most intractable cancers known and any success with pancreatic cancer is surprising in light of existing literature and art.

Pharmacological Compounds in this Invention

The science behind the combination is based on a triad of attacks in the biochemical cycles contributing to cancer cell replication.

Cancer cells must necessarily replicate for a "cancer" to thrive. Attacks on biochemical cycles at points where replication are involved are a favored approach. Cancer cells are particularly vulnerable to interference with lipid cell membrane status and ATP synthesis.

This invention proposes not only attack with a COX-2 inhibitor to interfere with the cyclooxygenase pathway, but by combination with lovastatin, focuses on another cycle, the formation of polyisoprenoids, particularly cholesterol.

The invention claims rofecoxib, but the principles stated are generally applicable to all selective COX-2 inhibitors. The meaning and definition of Cyclooxygenase-2 inhibitor ("COX-2 inhibitor" or "selective COX-2 inhibitor") in this invention shall include the following in this paragraph: all of the compounds and substances beginning on page 8 of Winokur WO99/20110 as members of three distinct structural classes of selective COX-2 inhibitor compounds, and the compounds and substances which are selective COX-2 inhibitors in Nichtberger, U.S. Pat. No. 6,136,804, Oct. 24, 2000, entitled "Combination therapy for treating, preventing, or reducing the risks associated with acute coronary ischemic syndrome and related conditions", and the compounds and substances which are selective COX-2 inhibitors in Isakson et al, PCT application WO/09641645 published Dec. 27, 1996, filed as PCT/US 9509905 on Jun. 12, 1995, entitled "Combination of a Cyclooxygenase-2

Inhibitor and a Leukotriene B4 Receptor Antagonist for the Treatment of Inflammations." The meaning of COX-2 inhibitor in this invention shall include the compounds and substances referenced and incorporated into Winokur WO99/20110 by reference to art therein, the compounds and substances referenced and incorporated into Nichtberger, U.S. Pat. No. 6,136,804, Oct. 24, 2000, by reference to art therein, and the compounds and substances which are COX-2 inhibitors referenced and incorporated into Isakson et al, PCT application WO/09641645 published Dec. 27, 1996, filed as PCT/US 9509905 on Jun. 12, 1995, entitled "Combination of a Cyclooxygenase-2 Inhibitor and a Leukotriene B4 Receptor Antagonist for the Treatment of Inflammations." The meaning of COX-2 inhibitor in this invention also includes rofecoxib, and celecoxib, marketed as VIOXX and CELEBREX by Merck and Searle/Pfizer respectively. Rofecoxib is discussed in Winokur, WO99/20110 as compound 3, on p.9. Celecoxib is discussed as SC-58635 in the same reference, and in T. Penning, Synthesis and biological evaluation of the 1,5-diarylpyrazole class of cyclooxygenase-2 inhibitors: identification of 4-[5-(4-methylphenyl)-3-(trifluoromethyl)-1H-pyrozol-1-yl] benzenesulfonamide (SC-58635, celecoxib)", J. Med. Chem. Apr. 25, 1997: 40(9): 1347–56. The meaning of COX-2 inhibitor in this invention also includes SC299 referred to as a fluorescent diaryloxazole. C. Lanzo et al, "Fluorescence quenching analysis of the association and dissociation of a diarylheterocycle to cyclooxygenasel-1 and cyclooxygenase-2: dynamic basis of cycloxygenase-2 selectivity", Biochemistry May 23, 2000 vol. 39(20) :6228–34, and in J. Talley et al, "4,5-Diaryloxazole inhibitors of cyclooxygenase-2 (COX-2)", Med. Res. Rev. May 1999; 19(3): 199–208. The meaning of COX-2 inhibitor in this invention also includes valdecoxib, See, "4-[5-Methyl-3-phenylisoxazol-1-yl]benzenesulfonamide, Valdecoxib: A Potent and Selective Inhibitor of COX-2", J. Med. Chem. 2000, Vol. 43: 775–777, and parecoxib, sodium salt or parecoxib sodium, See, N-[[(5-methyl-3-phenylixoxazol-4yl)-phenyl]sulfonyl]propanimide, Sodium Salt, Parecoxib Sodium: A Potent and Selective Inhibitor of COX-2 for Parenteral Administration", J. Med. Chem. 2000, Vol. 43: 1661–1663. The meaning of COX-2 inhibitor in this invention also includes the substitution of the sulfonamide moiety as a suitable replacement for the methylsulfonyl moiety. See, J. Carter et al, Synthesis and activity of sulfonamide-substituted 4,5-diaryl thiazoles as selective cyclooxygenase-2 inhibitors", Bioorg. Med. Chem. Lett Apr. 19, 1999: Vol. 9(8): 1171–74, and compounds referenced in the article "Design and synthesis of sulfonyl-substituted 4,5-diarylthiazoles as selective cyclooxygenase-2 inhibitors", Bioorg. Med. Chem. Lett Apr. 19, 1999: Vol. 9(8): 1167–70. The meaning of this invention includes a COX-2 inhibitor, NS398 referenced in two articles: Attiga et al, "Inhibitors of Prostaglandin Synthesis Inhibit Human Prostate Tumor Cell Invasiveness and Reduce the Release of Matrix Metalloproteinases", 60 Cancer Research 4629–4637, Aug. 15, 2000, and in "The cyclooxygenase-2 inhibitor celecoxib induces apoptosis by blocking Akt activation in human prostate cancer cells independently of Bcl-2," Hsu et al, 275(15) J. Biol. Chem. 11397–11403 (2000). The meaning of COX-2 inhibitor in this invention includes the cyclo-oxygenase-2 selective compounds referenced in Mitchell et al, "Cyclo-oxygenase-2: pharmacology, physiology, biochemistry and relevance to NSAID therapy", Brit. J. of Pharmacology (1999) vol.128: 1121–1132, see especially p. 1126. The meaning of COX-2 inhibitor in this invention includes so-called NO-NSAIDs or nitric oxide-releasing-NSAIDs referred to in L. Jackson et al, "COX-2 Selective Nonsteriodal Anti-Inflammatory Drugs: Do They Really Offer Any Advantages?", Drugs, June, 2000 vol. 59(6): 1207–1216 and the articles at footnotes 27, and 28. Also included in the meaning of COX-2 inhibitor in this invention includes any substance that selectively inhibits the COX-2 isoenzyme over the COX-1 isoenzyme in a ratio of greater than 10 to 1 and preferably in ratio of at least 40 to 1 as referenced in Winokur WO 99/20110, and has one substituent having both atoms with free electrons under traditional valence-shell-electron-pair-repulsion theory located on a cyclic ring (as in the sulfylamine portion of celecoxib), and a second substituent located on a different ring sufficiently far from said first substituent to have no significant electron interaction with the first substituent. The second substituent should have an electronegativity within such substituent greater than 0.5, or the second substituent should be an atom located on the periphery of the compound selected from the group of a halogen F, Cl, Br or I, or A group VI element S or O. Thus for purposes of this last included meaning of a COX-2 inhibitor, one portion of the COX-2 inhibitor should be hydrophilic and the other portion lipophilic. Also included as a COX-2 inhibitor are compounds listed at page 553 in Pharmacotherapy, $4^{th}$ ed: A Pathophysiologic Approach, Depiro et al (McGraw Hill 1999) including nabumetone and entodolac. Recognizing that there is overlap among the selective COX-2 inhibitors set out in this paragraph, the intent of the term COX-2 inhibitor is to comprehensively include all selective COX-2 inhibitors, selective in the sense of inhibiting COX-2 over COX-1. The package inserts for rofecoxib and celecoxib are attached and adopted herein by reference. The inventors add to the class of COX-2 inhibitors useful in the invention the drug bearing the name etoricoxib referenced in the Wall Street Journal, Dec. 13, 2000 manufactured by Merck. See, also, Chauret et al, "In vitro metabolism considerations, including activity testing of metabolites, in the discovery and selection of the COX-2 inhibitor etoricoxib (MK-0663)," Bioorg. Med. Chem. Lett. 11(8): 1059–62 (Apr. 23, 2001). Another selective COX-2 inhibitor is DFU [5,5-dimethyl-3-(3-fluorophenyl)-4-(4-methylsulphonyl) phenyl-2(5H)-furanone] referenced in Yergey et al, Drug Metab. Dispos. 29(5):638–44 (May 2001). The inventors also include as a selective COX-2 inhibitor the flavonoid antioxidant silymarin, and an active ingredient in silymarin, silybinin, which demonstrated significant COX-2 inhibition relative to COX-1 inhibition. The silymarin also showed protection against depletion of glutathione peroxidase. Zhao et al, "Significant Inhibition by the Flavonoid Antioxidant Silymarin against 12-O-tetracecanoylphorbol 13-acetate-caused modulation of antioxidant and inflammatory enzymes, and cyclooxygenase 2 and interleukin-1 alpha expression in SENCAR mouse epidermis: implications in the prevention of stage I tumor promotion," Mol. Carcinog. December 1999, Vol 26(4):321–33 PMID 10569809. Silymarin has been used to treat liver diseases in Europe.

The term COX-2 inhibitor includes all pharmaceutically acceptable salts for the COX-2 inhibiting compound selected. Examples of such salt forms of COX-2 inhibitors include but are not limited to salts derived from inorganic bases including aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occuring substituted amines, cyclic amines, and basic ion exchange resins, such as arginine, betaine, caffeine, choline, N,N-dibenzylethylenediamine, diethylamide, 2-diethylaminoethanol, 2-dimethylaminoethanol, ethanolamine, ethylenediamine, N-ethylmorpholine, N-ethylpeperidine, glutamine, glucosamine, histidine, hydrabamine, isopropylamine, lysine, methyglucamine, morpholine, piperazine, piperidine, polyamine resins, procaine, purine, theobromine, triethylamine, trimethylamine, triporopylamine, troethamine, and the like.

The HMG-CoA reductase inhibitor claimed in this invention is lovastatin. The principles of this invention are generally applicable to all statins. The meaning and definition of a 3-hydroxy-3-methylglutaryl-Coenzyme-A reductase inhibitor of ("HMG-CoA inhibitor") in this invention is any selective, competitive inhibitor of HMG-CoA reductase, the rate-limiting enzyme that converts HMG-CoA into mevalonate, generally referred to as cholesterol-lowering statins, and includes 1) lovastatin, marketed under the trademark MEVACOR by Merck, and described, among other places in U.S. Pat. No. 4,231,938,
2) simvastatin, marketed under the trademark ZOCOR by Merck, and described, among other places in U.S. Pat. No. 4,444,784,
3) pravastatin, marketed under the trademark PRAVACOL by Bristol-Myers-Squibb, and described, among other places, in U.S. Pat. No. 4,346,227,
4) atorvastatin calcium, marketed under the name LIPITOR by Parke-Davis, and described, among other places, in U.S. Pat. No. 5,273,995,
5) cerivastatin sodium, marketed under the name BAYCOL, by Bayer, and described, among other places, in U.S. Pat. No. 5,177,080, and
6) fluvastatin sodium, marketed under the name LESCOL, by Novartis Pharmaceuticals, and described, among other places, in U.S. Pat. No. 5,354,772.

The term HMG-CoA inhibitor (used as shorthand for and also referred to as "HMG-CoA reductase inhibitor") further includes all HMG-CoA reductase inhibitors described in Winokur, PCT Appl. US98/21901, filed Oct. 16, 1998, published as WO99/20110 entitled Combination Therapy for Reducing the Risks Associated with Cardio and Cerebrovascular Disease," and the compounds and substances which are HMG-CoA inhibitors in Nichtberger, U.S. Pat. No. 6,136,804, Oct. 24, 2000, entitled "Combination therapy for treating, preventing, or reducing the risks associated with acute coronary ischemic syndrome and related conditions." The meaning of HMG-CoA inhibitor in this invention shall include the compounds and substances referenced and incorporated into Winokur WO99/20110 by reference to art therein, and the compounds and substances referenced and incorporated into Nichtberger, U.S. Pat. No. 6,136,804, Oct. 24, 2000, by reference to art therein. Compactin is also described as a fungi derived competitive inhibitor of HMG-CoA reductase. Lehninger, Principles of Biochemistry (3$^{rd}$ ed. 2000) at 811. An HMG-CoA reductase inhibitor, with the natural structure of lovastatin identical to the synthetic structure of lovastatin, can also be isolated from red rice yeast or the rice in sufficient quantity an may be an HMG-CoA reductase inhibitor. The red rice yeast is found as cholestin or cholestol and is available on the Internet from a variety places including China Beijing Jingxin Biochemical Products Factor, Linxiao Rd. S., Daxing Count, Beijing, PRC or its U.S. agent PHC Resources, Inc., 77 Milltown Rd., East Brunswick, N.J. 08816. The red rice yeast is referred to in an FDA warning letter of May 8, 2001 to Maypro Industries available at www.fda.gov/foi/warning_letters/g1249d.pdf.

Based on the pharmaceutical product description of Merck for simvastatin, which description is adopted herein and attached for reference, and which drug is marketed as ZOCOR, a registered trademark of Merck, simvastatin functions in a similar way to lovastatin, another drug marketed by Merck under the registered trademark of MEVACOR, the pharmaceutical product description for which is adopted herein and attached for reference. Both are derived from *aspergillus terreus*.

Recognizing that there is overlap among the HMG-CoA inhibitors set out in this paragraph and in the list of six HMG-CoA inhibitors set forth above, the intent of the term HMG-CoA inhibitor is to comprehensively include all HMG-CoA inhibitors.

The term HMG-CoA inhibitor encompasses the pharmaceutically acceptable salts of HMG-CoA inhibitor selected. The invention includes pharmaceutically active salts of an HMG-CoA inhibitor, which may include non-toxic salts of the compounds employed in this invention which are generally prepared by reacting the free acid with a suitable organic or inorganic base. Examples of salt forms of HMG-CoA reductase inhibitors may include, but are not limited to, acetate, benzenesulfonate, benzoate, bicarbonate, bisulfate, bitartrate, borate, bromide, calcium, camsylate, carbonate, chloride, citrate, dihydrochloride, edentate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laureate, malate, maleate, mandelate, mesylate, methylbromide, methylnitrate, methylsulfate, mutate, napsylate, mitrate, oleate, oxalate, pamaote, palpitate, panthothenate, phosphate/diphosphate, polygalacturonate, potassium, sodium, stearate, subacetate, succinate, tannate, tartrate, teoclate, tosylate, triethiodide, and valerate. The principles are also applicable to the inclusion of an additional ingredient, namely an edible resin that binds bile acids and prevents their reabsorption from the intestine, though this is not the preferred mode. Lehninger, Principles of Biochemistry (3$^{rd}$ ed. 2000) at 811.

Ester derivatives of the above described compounds included HMG-CoA inhibitors may act as prodrugs which, when absorbed into the bloodstream of a warm-blooded animal, may cleave in such a manner as to release the drug form and permit the drug to afford improved therapeutic efficacy.

The package inserts for COX-2 inhibitors and HMG-CoA inhibitors attached to the provisional application No. 60/245,592 and the description in the patents and methods in those patents related to the selective COX-2 inhibitors and HMG-CoA inhibitors are adopted by reference.

Cystine will be used as a generic reference for a glutathione pathway enhancing and detoxifying compound. Such compounds include the following:

Cystine is (3,3'-dithiobis [2-aminopropanoic acid]). Cystine is readily reduced to cysteine. Cystine is present in most mammalian hair and keratin.

Cysteine is 2-amino-3-mercapto propanoic acid. It is readily converted by oxioreduction to cystine. It is a constituent of glutathione and abundantly present in the metallothioneines.

Cystine in the body-useful form as L-cystine is available from Spectrum Chemical Mfg. Corp. 14422 S. San Pedro St., Gardena, Calif. 90248.

Cystine, cysteine, and N-Acetyl cysteine and pharmaceutically acceptable salts, including the pharmaceutically active forms described in Kozhemyakin et al, published by WIPO as WO 00/031120, PCT/RU99/00453, filed internationally on Nov. 19, 1999, "Hexapeptide with the Stabilized Disulfide Bond and Derivatives Thereof Regulating Metabolism, Proliferation, Differentiation and Apoptosis," will all collectively be referred to as cystine in this invention. Included in the term cystine is also any therapeutically beneficial sulfur donating compound, including ebselen, which interacts with the glutathione pathway. The invention contemplates in the term cystine undenatured whey protein products designed to have enhanced cystine concentration as well as protein products which contain cysteine and cystine. They can be in the form of food products. Immunocal® whey protein diet supplement by Immunotek Research Ltd. of Montreal Quebec is a useful product with cystine.

The addition of cystine, cysteine, N-acetyl cysteine, or the pharmaceutically acceptable salt of those substances yields another effect in this invention not facially evident from the independent properties of the basic components of the invention. Administration of a glutathione pathway enhancing and detoxifying compound, preferably cystine, which has the best and most rapid upload into the glutathione pathway and better storage capability by the body, or N-acetyl cysteine, enhances the immune system competency of the patient. Lipoic acid can be an adjunct to the cystine.

All of these cystine and cystine-like compounds function as a glutathione pathway enhancing and detoxifying compound. They have the additional benefit of ameliorating the negative renal, hepatic and gastric effects of COX-2 inhibitors and HMG-CoA inhibitors, both as a combination and individually. The enhancement of the glutathione level and pathway has a second important and unexpected effect. The avoidance of a glutathione deficiency steers the patient to have a higher Th-1 response to Th-2 response ratio than the patient would have with any glutathione deficiency

DESCRIPTION OF INVENTION

The preferred mode of invention without limiting its use or use of pharmaceutical equivalents to those described herein is to administer a therapeutic dose of a cyclooxygenase-2 inhibitor, namely VIOXX (a registered trademark of Merck Co. for a drug formally known as rofecoxib) (referred to as a "COX-2 inhibitor"), in combination with a therapeutic dose of a 3-hydroxy-3-methylglutaryl-Coenzyme-A reductase inhibitor, namely with Mevacor (a registered trademark of Merck Co. for a drug formally known as lovastatin) ("HMG-CoA inhibitor") starting with the minimum recommended doses of each drug on the package inserts attached to provisional applications Nos. 60/283,486 and 60/245,592. For patients who have advanced prostate cancer whose PSA does not respond to the combination, the dosage should be increased in step wise fashion to the maximum dose in the therapeutic window. The preferred mode of so doing is to monitor the patient each six weeks. A person of ordinary skill in the medical arts can apply the regimen described in this specification.

The inventors suggest measuring at least cholesterol level and isoprostane level. If a patient's cholesterol level is decreasing, then the HMG CoA inhibitor is affecting cholesterol synthesis. If isoprostane levels are rising, then the COX-2 inhibitor should be having an effect. The lack of change in one or the other suggests that the medication to achieve the desired metabolic pathway effect should be adjusted.

Another way to test for effectiveness and enable dosage adjustment is to test cytokine levels. Once at least two inflammatory response markers show therapeutic change then the combination should be having an effect. The preferred markers include upregulation of IL-12 and down-regulation of IL-10. "Specific inhibition of cyclooxygenase restores anti-tumor reactivity by altering balance of IL-10 and IL-12 synthesis", J. Immunol 2000 vol 164(1) :361–370 [increased COX-2 expression increases PGE-2 which induces IL-10; accordingly, use of COX-2 inhibitor leads to down-regulation of IL-10; also observed concomitant upregulation of IL-12]. Testing of cytokines involves the use of ELISA assays to determine cytokine levels. Chemoluminescence tests are also used for certain interleukins. Other useful inflammatory response markers that may be tested include:

| Test/ | FactorName/range | Brief description |
|---|---|---|
| CRP | C-reactive protein | General inflammatory response marker, downregulation indicates amelioration of inflammatory response mechanism |
| IL-10 | Interleukin-10 $ED_{50} = 0.5$ ng–1 ng/mL | Potent blocker of activation of cytokine synthesis and several accessory functions of macrophages; produced in CD$+ T cells and T cell clones, and other cells; downregulation indicates lessened interference with cytokine synthesis of cytokines needing upregulation and lessened macrophage activity interference |
| IL-2 | Interleukin-2 0.0–4.0 pg/mL | Activates lymphocytes, potent stimulator of cytokine activated killer cells (LAK's) which demonstrate enhanced MHC non-restricted cytotoxicity. Used for renal cell CA-encourage Tc1 activity |
| IL-6 | Interleukin-6 0.0–149 pg/mL | Involved in T-cell activation; in nesting cells induce the expression of receptors for T-cell growth factor. Very important in inducing B-cells to differentiate into antibody-forming cells. In liver, it stimulates production of acute phase proteins. Growth factor for multiple myeloma |
| IL-8 | Interleukin-8 0.0–70 pg/mL | Proinflammatory cytokine released from range of cells including monocytes, endothelial cells, epithelial cells, hepatocytes, fibroblasts and chondrocytes |
| IL-12 | Interleukin-12 Range 0.7 pg/mL–7000 pg/mL | Potent initial stimulus for T-and Nk-cell, IFN(IFN = interferon)-γ production. May encourage Tc1 generation. Potentiates NK cell to release IFN-8. Works in a manner complementary to IL-10; increase in level compared to baseline indicates potential for increased cell-mediated response |
| TNF | Tumor Necrosis Factor 0.0–4.9 pg/mL | Activates macrophage (mφs) and neutrophils |
| IFN-γ | Interferon-gamma 0.0–1.5 pg/mL | Encourages Tc1 generation role in early phase of immune response including antiviral and antiproliferative properties |
| IFN-α | Interferon-alpha 0.0–1.5 pg/mL | Induces IL-2 and can be used to switch Th cells from a Th2 to a Th1 profile |
| ECP | Eosinophilic cationic protein 1.5–5.5 mg/mL | Potent indicator of eosinophilic degranulation resulting in a wide range of inflammatory conditions: autoimmune disease, bronchial asthma, parasitic infections, viral infections |
| IL-10 | Interleukin-10 $ED_{50} = 0.5$ ng–1 ng/mL | Potent blocker of activation of cytokine synthesis and several accessory functions of macrophages; produced in CD$+ T cells and T cell clones, and other cells; downregulation indicates lessened interference with cytokine synthesis of cytokines needing upregulation and lessened macrophage activity interference |

Advanced prostate cancer particularly refers to prostate cancer that has not been successfully treated by surgery, chemotherapy, radiation and/or androgen suppressant(s).

The preferred mode of invention without limiting its use or use of pharmaceutical equivalents to those described herein is to use VIOXX (a registered trademark of Merck Co. for a drug formally known as rofecoxib) in combination with Mevacor (a registered trademark of Merck Co. for a drug formally known as lovastatin) for the treatment of prostate cancer.

The invention retards or drives prostate cancer into remission, best illustrated by lowering the Prostate Specific Antigen, the standard measure of prostate cancer activity in the human body.

The method of the invention is the step of administering the combination of COX-2 inhibitor and HMG-CoA inhibitor, particularly lovastatin and rofecoxib, or the combined sequence of steps of sequentially administering the COX-2 inhibitor and HMG-CoA inhibitor, particularly lovastatin and rofecoxib. An alternative of this method of the invention is the combined sequence of steps of sequentially administering the COX-2 inhibitor and HMG-CoA inhibitor, particularly lovastatin and rofecoxib.

Another preferred method is the step of administering the combination of COX-2 inhibitor, HMG-CoA inhibitor, particularly lovastatin and rofecoxib, along with cystine as a glutathione pathway enhancing and detoxifying compound. An alternative of this method of the invention is the combined sequence of steps of sequentially administering the COX-2 inhibitor and HMG-CoA inhibitor, particularly lovastatin and rofecoxib, along with cystine as a glutathione pathway enhancing and detoxifying compound.

Also part of the invention is the method of manufacturing a combination of a COX-2 inhibitor and a 3-hydroxy-3-methylglutaryl-Coenzyme-A reductase inhibitor, namely manufacturing a combination of lovastatin and rofecoxib. Also part of the invention is the method of manufacturing a combination of a COX-2 inhibitor, a 3-hydroxy-3-methylglutaryl-Coenzyme-A reductase inhibitor, namely manufacturing a combination of lovastatin and rofecoxib, along with cystine as a glutathione pathway enhancing and detoxifying compound.

Thus, the prior discussion reviews one preferred mode of the invention, a COX-2 inhibitor and an HMG-CoA inhibitor. Another mode of the invention includes a COX-2 inhibitor and an HMG-CoA inhibitor, namely rofecoxib and lovastatin and cystine or another glutathione pathway enhancing compound. As ATP and cholesterol synthesis is being affected in the cancer cell, cystine is being used to enhance the immune system competency and assist normal cells, through the glutathione pathway, in maintaining their stability.

The combination of a COX-2 inhibitor and an HMG-CoA inhibitor could also be used as an aborfacient.

The invention also can utilize one or more of certain additional active agents in combination with the HMG-CoA inhibitor and COX-2 inhibitor, or in combination with the HMG-CoA inhibitor, COX-2 inhibitor, and cystine. The additional active agents can be in a single dosage formulation, or may be administered to the patient in a separate dosage formulation, which allows for concurrent or sequential administration. Examples of additional active agents which may be employed include squalene epoxidase inhibitors, squalene synthase inhibitors, probucal, glycoprotein IIb/IIIa fibrinogen receptor antagonists, and pharmaceutically acceptable salts of those additional active agents which do not interfere with the HMG-CoA inhibitor and COX-2 inhibitor combination and method or with the HMG-CoA inhibitor, COX-2 inhibitor, and cystine. These and pharmaceutically equivalent agents in the same classes are described in the cited Winokur art, PCT Appl. US98/21901, filed Oct. 16, 1998, published as WO99/20110 entitled "Combination Therapy for Reducing the Risks Associated with Cardio and Cerebrovascular Disease" and in Nichtberger, U.S. Pat. No. 6, 136,804, Oct. 24, 2000. The therapeutically effective amount to use for these additional active agents is referred to in the just-cited art, can be seen in the Physician Desk Reference (PDR) 2001, and may be seen on the package inserts.

The instant pharmaceutical combination comprising an HMG-CoA inhibitor in combination with a COX-2 inhibitor and cystine includes administration of a single pharmaceutical dosage formulation which contains both the HMG-CoA inhibitor and the COX-2 inhibitor and cystine, as well as administration of each active agent in its own separate pharmaceutical dosage formulation. A cystine supplement taken at a different time of day may be a separate dose without the HMG-CoA inhibitor or the COX-2 inhibitor. Cystine is the suggested glutathione pathway enhancing and detoxifying compound. The amount of cystine to be included in an oral dosage combination is a therapeutically effective amount to reach normal glutathione levels. Such therapeutically effective amount should preferably and initially be 140 mg/70 Kg man twice per day.

Where separate dosage formulations are used, the HMG-CoA inhibitor and the COX-2 inhibitor can be administered at essentially the same time, i.e., concurrently, or at staggered intervals, i.e., sequentially. Without the cystine, the instant pharmaceutical combination comprising an HMG-CoA inhibitor in combination with a COX-2 inhibitor includes administration of a single pharmaceutical dosage formulation which contains both the HMG-CoA inhibitor and the COX-2 inhibitor, as well as administration of each active agent in its own separate pharmaceutical dosage formulation. The instant pharmaceutical combinations are understood to include all these regimens. Administration in these various ways is suitable for the present invention as long as the beneficial pharmaceutical effect of the HMG-CoA inhibitor and the COX-2 inhibitor are realized by the patient at substantially the same time. Such beneficial effect is preferably achieved when the target blood level concentrations of each active drug are maintained at substantially the same time. It is preferred that the HMG-CoA inhibitor and the COX-2 inhibitor be co-administered concurrently on a once-a-day dosing schedule; however, varying dosing schedules, such as the HMG-CoA once per day and the COX-2 inhibitor once, twice or more times per day, is also encompassed herein. In all courses of administration, the therapeutic doses for cystine can be added, and likely necessitate an additional therapeutic dose early in the administration regimen. As much as possible, a single oral dosage formulation is preferred. A single dosage formulation will provide convenience for the patient, which is an important consideration especially for patients who may be in need of multiple medications. Administration of the HMG-CoA inhibitor or COX-2 inhibitor can be by tablet, liquid suspension, or many other pharmaceutically acceptable carriers known by or used by reasonably skilled practitioners in the art of pharmacology or pharmacological manufacturing including by the combinations and methods in the cited Winokur art, PCT Appl. US98/21901, filed Oct. 16, 1998, published as WO99/20110 entitled "Combination Therapy for Reducing the Risks Associated with Cardio and Cerebrovascular Disease" and in Nichtberger, U.S. Pat. No. 6,136,804, Oct. 24, 2000.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. The active drugs may also be delivered by the use of monoclonal antibodies as individual carriers to which the compound molecules are coupled. They may also be coupled with soluble polymers as targetable drug carriers. Such polymers can include polyvinylpyrrolidone, pyran copolymer, polyhydroxy-propyl-methacrylamide-phenol, polyhydroxy-ethyl- aspartamide-phenol, or polyethyleneoxide-polylysine substituted with palmitoyl residues. Furthermore, the active drugs may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. All of these are described in Nichtberger, U.S. Pat. No. 6,136,804, Oct. 24, 2000.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A therapeutic change is a change in a measured biochemical characteristic in a direction expected to alleviate the disease or condition being addressed. The term "prophylactically effective amount " is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The term "therapeutic window" is intended to mean the range of dose between the minimal amount to achieve any therapeutic change, and the maximum amount which results in a response that is the response immediately before toxicity to the patient.

The dosage regimen utilizing an HMG-CoA inhibitor in combination with COX-2 inhibitor is selected in accordance with a variety of factors including type, species, age, weight, sex and medical condition of the patient; the severity of the condition to be treated; the route of administration; the cardiac, renal and hepatic function of the patient; and the particular compound or salt or ester thereof employed. Dosages in all events should be limited to the therapeutic window. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective amount.

Discussion of Pharmakinetics and Summary of Literature

The literature has suggested that an HMG-CoA reductase inhibitor may separately have efficacy toward cancers, and that a selective COX-2 inhibitor may separately have efficacy toward certain cancers, but no literature suggests that the substances be combined to treat cancer.

In drawing conclusions concerning the pharmakinetics, the inventors observe that an intriguing and surprising aspect of the invention, which suggests many of the pharmakinetics, is that quality of life is not substantially affected by the treatment; the patient is alive, the patient does not die; at the same time, at least in the short term, the cancer is also present albeit repressed in its activity. The consideration of pharmakinetics attempts to comprehend these combined phenomena.

An important aspect of the pharmakinetics is the selectivity to cancer cells and essentially microadministration of cancer therapy. For instance, this invention proposes to affect ubiquinones in important ways. There is art emerging, subsequent to provisional application No. 60/263,486, to a pending trial of Ubiquinone under a trade name of Ubigel by Gel-Tec, Drug Facts and Comparisons, 55$^{th}$ ed. 2001 at KU-16 (Publ. by Facts & Comparisons 2000). Ubiquinone or CoQ-10 administration, in itself, is not likely have the benefits of the present invention because it is proposed to be administered by macroadministration to the entire organism, either orally or intravenously or in the general vicinity of the tumor area.

By contrast to such effort at macroadministration, this invention proposes virtual selective-to-cancer microadministration utilizing the body's own metabolic mechanisms and responses. This is a unique aspect of this invention and an important concept behind the invention. The inventors propose that one of the dilemmas of cancer therapy is to deliver the needed dose to the right place and minimize harm when the therapy is not in the right place.

The inventors believe that the most optimal treatments involve the utilization of the biochemical physiologic machine of the body, and preferably of the individual cell, to construct, manufacture and adjust the individual cell chemistry to achieve the desired object: in the case of the cancer cell or other afflicted and undesired cell, to disrupt its mechanisms of replication, primarily by focusing on the energy mechanism of the cell with the corollary result of interfering with membrane synthesis and cell replication, and in many instances, as the cell struggles to reach homeostasis, inducing apoptosis.

In sum, by interfering with the cyclooxygenase pathway, particularly important in the formation of prostaglandins, and thus in the cell-signaling mechanism critical for replication of cancer cells, by directly interfering, using an HMG-CoA inhibitor, namely lovastatin, with polyisoprenoid formation and disorienting the feedback regulation system in that formation cycle, and later in that cycle, by utilizing a COX-2 inhibitor, preferably rofecoxib, to further inhibit the formation of cholesterol, the invention renders cancer cells vulnerable to poor replication and subject to bodily defenses, thus slowing the cancer activity, and in the instance of prostate cancer, lowering the PSA of the patient while destroying cancer cells.

The COX-2 Inhibitor and the Cycloxygenase-prostaglandin Pathway

The COX-2 inhibitor interferes with the operation of the cyclooxygenase cycle from which are generated prostaglandins critical in cell division chemistry. Direct inhibition occurs of the synthesis of COX-2, a precursor of prostaglandins. Biochemistry, Geigy Scientific Tables, Book 4, ed. by C. Lemtner, published by Ciba-Geigy (1986) ISBN-0-91-4168-53-3, Lib. Cong. Cat. No. 81-70045 pp. 25–27 attached to Prov. Appl. No. 60/245,592, the text of which attachment is adopted by reference herein). This effect has been discussed in the literature. Fosslien, "Biochemistry of Cyclooxygenase (COX)-2 Inhibitors and Molecular Pathology of COX-2 in Neoplasia," Crit. Rev. in Clin. Lab. Sci. 37(5): 431–502 (November 2000). As also previously referenced, COX-2 inhibitors were reported to be inhibiting certain cancers, particularly familial adenomatous polyposis. See, 319 (7218) British Medical Journal 1155 (Oct. 30, 1999). COX-2 inhibitors, in that instance, celecoxib, a COX-2 inhibitor manufactured by G. D. Searle, and sold under the brand name Celebrex, had caused a reduction in adenomatous polyps which are a virtual guarantor of cancer of the colon if left untreated. Cyclooxygenase-2 had been implicated in colorectal cancer and colonic tumorigenesis. See, "The Relationship Between Cyclooxygenase-2 Expressions and Colorectal Cancer", 282(13) J. Amer. Med. Ass'n:1254–1257 (Oct. 6, 1999).

Both celecoxib and rofecoxib are suggested to have similar effects. See Vol. 56(2) Amer. J. of Health-System Pharmacy: 106–107 (Jan. 15, 1999).

One of the clear benefits of the selective COX-2 inhibitor is that COX-1 isoenzymes have what has been characterized as having general housekeeping functions generally ameliorative to bodily health. Fosslien, "Biochemistry of Cyclooxygenase (COX)-2 Inhibitors and Molecular Pathology of COX-2 in Neoplasia," Crit. Rev. in Clin. Lab. Sci. 37(5): 431–502 (November 2000). Aspirin, a classic COX inhibitor, also inhibits COX-1, thereby achieving anti-inflammatory effect, for which aspirin is well-known, at the cost of beneficial aspects of COX-1 isoenzymes. Thus, a COX-2 inhibitor that is selective is important in the invention.

A selective COX-2 inhibitor is important to this cancer management invention, but as the literature indicates, does not provide a comprehensive answer nor a comprehensive cancer response.

The COX-2 Inhibitor and Angiogenesis

In mice, a COX-2 inhibitor, NS398, was reported to inhibit angiogenesis of a prostate cancer specimen in vivo. Liu et al, "Inhibition of Cyclooxygenase-2 suppresses Angiogenesis and the Growth of Prostate Cancer in Vivo," 164 J. of Urology 820–825 (September 2000) at 820.

Inhibition of Cholesterol Synthesis by COX-2 Inhibitor and HMG-CoA Inhibitor

In viewing the biochemical cycle through which the formation of polyisoprenoids occurs, there are a series of intermediates. See, Biochemistry, Geigy Scientific Tables, Book 4, ed. by C. Lemtner, published by Ciba-Geigy (1986) ISBN-0-91-4168-53-3, Lib. Cong. Cat. No. 81-70045 pp. 25–27, 142–147 (attached to Prov. Appl. No. 60/245,592, the text of which attachment is adopted by reference herein). A key end product of the biochemical cycle of formation of polyisoprenoids is cholesterol. In order for a cell to replicate successfully, the entire cholesterol cycle must be functioning properly and cholesterol is especially critical to membrane stabilization, a necessary ingredient for successful cancer cell replication.

The "Early" Cholesterol Pathway: Acetyl CoA to Mevalonate

Examining the intermediates in the polyisoprenoid formation cycle carefully, beginning with Acetyl-CoA, the next intermediate is 3-Hydroxy-3-methylglutaryl-CoA ("HMG-CoA"). There is a feed back regulation mechanism immediately after this intermediate before transition occurs to the next intermediate: Mevalonate. Salway, Metabolism at a Glance, 88–89 (Blackwell Science $2^{nd}$ ed. Oxford 1999). The invention proposes to use lovastatin as an HMG-CoA reductase inhibitor. An HMG-CoA reductase inhibitor interferes in the polyisoprenoid formation cycle, and particularly interferes with cell wall synthesis, thereby interfering with a necessary construct of cancer replication. Because ATP cycle intermediaries are juxtaposed to the HMG-CoA feed-back mechanism, and ATP and ATP cycle intermediaries are apparent in transition steps of biosynthesis of cholesterol subsequent to the Mevalonate intermediate, the effect of a cancer cell starved of necessary cholesterol is to biochemically invite increased production of intermediates in the transition from mevalonate to cholesterol, and to biochemically invite increased production of HMG-CoA, whose biosynthesis is being inhibited. Such increased production draws on the ATP and ATP cycle intermediaries in the cancer cell.

The Later Cycle: Squalene to Cholesterol Synthesis

Continuing examination of the polyisoprenoid formation cycle, after the Mevalonate intermediate, the cycle continues with the formation of isopentenyl diphosphate, and then farnesyl diphosphate. Three intermediate products emerge after the farnesyl diphosphate intermediary: squalene, dolichols and ubiquinone. Salway, Metabolism at a Glance at 88–89, (Blackwell Science 2nd ed Oxford 1999).

A second effect cooperates with the HMG-CoA inhibitor to exacerbate the energy drain on a cancer cell. This collateral effect is additional to the effect of a COX-2 inhibitor on the cyclooxygenase cycle. While the HMG-CoA inhibitor has decreased the production of the subsequent intermediates to farnesyl pyrophosphate, the COX-2 inhibitor, because of the active electron field substituents, also interferes in a way not discussed in the literature with the normal biochemistry of squalene to cholesterol synthesis. Squalene transitions through a complex series of intermediates to cholesterol. This interference in the biosynthesis pathway subsequent to squalene synthesis further disables the cell division chemistry of a cancer cell and leaves it vulnerable to apoptosis. Notably, the transition states from squalene to cholesterol between intermediaries depend on critical inputs of ATP cycle chemicals, including NADP and NADPH. Salway, Metabolism at a Glance at 88–89, Blackwell Science 2d ed 1999). A COX-2 inhibitor interferes with, but does not appear to stop, synthesis of certain of these intermediaries. This either results in insufficient cholesterol for cancer cell replication or results in introduction of further drain on the ATP cycle chemicals to produce the desired cholesterol critical for cell replication. This drain on the ATP cycle is beyond the stresses already imposed by the HMG-CoA inhibitor. As the replicating cell has further need for cholesterol, further energy is diverted from the cell.

The "Middle" of the Cholesterol Synthesis Cycle: Farnesyl Pyrophosphate and Ubiquinones A corollary effect of the partial inhibition of the production of cholesterol from squalene and the triggering of increased production of farnesyl pyrophosphate is that relatively more ubiquinones are produced which are not being inhibited in the same manner as the squalene to cholesterol synthesis is inhibited.

Ubiquinones are key participants in the Q cycle in mitochondrial respiration. With the relative overproduction of ubiquinone that occurs in order to attempt to produce the requisite cholesterol for cell replication, one of two effects, or both effects, occur on mitochondrial respiration.

The replicating cancer cell either comes under osmotic pressure to decrease the concentration of ubiquinone, or the increased ubiquinone concentration changes the electron transport mechanism in the inner membrane of the mitochondria. If the cell admits fluid to stabilize the ubiquinone concentration, the cell must normally change size or shape to do so. Ellerby et al, Measurement of Cellular Oxidation, Reactive Oxygen Species, and Antioxidant Enzymes during Apoptosis, 322 Method in Enzym. 413 (Academic Press 2000), Bortner, Volume Regulation and Ion Transport during Apoptosis, 322 Method in Enzym. 421 (Academic Press 2000).

If the increased ubiquinone concentration changes the electron transport mechanism, the predicted effect is that there is a change in electron transfer from Complex 1 toward Complex 3. See Metabolism at a Glance, J. G. Salway, p. 12–15 (Blackwell Science Ltd., Oxford and London, 2$^{nd}$ ed. 1999).

Simultaneous to the ubiquinone effect, giving attention to both the COX-2 inhibitor with the hydrophilic and lipophilic substituents referred to earlier in this specification and the chemical potential of the unpaired electrons on the first and second substituents, the electrochemical potential and gradient between the matrix side of the membrane and the opposite side membrane is changed, which affects the proton pump and migration of H$^+$ ions and in turn interferes with ATP synthesis. The likely reason is one of several, or a combination of several reasons. The COX-2 inhibitor, by changing the electrochemical gradient and potential across the membrane inhibits the potential need for ATP synthesis. Further, the electron attraction to the H+ cations on the matrix side, likely from the O=S=O bond in rofecoxib (or celecoxib), either slows the cation, potentially bonds and neutralizes them, or if an excess of electrons pushed by the ubiquinone shuttle from complex II to complex III encounters the cations, they potentially neutralize the H+ cations.

The cancer cell has an opportunity to again change the concentration to proper levels, but another osmotic pressure is generated. Any disruption in ion transport that produces excess cytochrome would either be potentially fatal to the cell, or require yet another osmotic effect. Bortner suggests a volume loss or movement of ions is associated with cell apoptosis. "Cell volume is normally controlled within narrow limits." Bortner, 322 Methods in Enzym. 422. Ellerby associates any change in cell size as either a coincident event to apoptosis or a precursor to completion of apoptosis phases. Ellerby, 322 Methods in Enzym. at 413–415. Bortner proposes the thesis that "When cells are placed in a hypertonic environment, shrinkage occurs because of the loss of osmotically obligated water. However, over a period of time diverse cell types compensate for the volume loss by activating a regulatory volume increase (RVI) response. This response allows for an influx of ions, with the concomitant movement of water into the cells to achieve a near-normal size." Bortner, 322 Methods in Enzym. 422. Thus, there is movement of osmotically obligated water from the cell [or to the cell] to achieve a near normal cell size. If not successful, excess cytochrome has been implicated in the generation of caspases which often lead to cell apoptosis. Ellerby, 322 Methods in Enzym. 413–415.

Thus, the novel combination for retarding cancer does so in part by producing osmotic stress selectively in cancer cells, and in part by interfering with membrane synthesis in cancer cells. Movement of any osmotically obligated fluid has a corollary effect of also speeding into replicating cells potentially detrimental biochemicals from the body's own immune system. Another corollary of any change in electrochemistry in the area of the matrix or the size of the cell is damage to ion transport channels, the blockage or overexpansion of which ion transport channel is often fatal to the cell. Ellerby, 322 Methods in Enzym. 413–421, Bortner, 322 Methods in Enzym. 421–433. The result of mitochrondrial respiration uncoupling has been observed in conjunction with non-steriodal anti-inflammatory drugs. Fosslien, "Biochemistry of Cyclooxygenase (COX)-2 Inhibitors and Molecular Pathology of COX-2 in Neoplasia," Crit. Rev. in Clin. Lab. Sci. 37(5): 431–502, pp. 453–455 (November 2000).

Since cancer replication is very sensitive to ATP cycle disruptions, the effect is to divert cell energy "unnecessarily" to attempting to overcome the effect of the HMG-CoA inhibitor and the COX-2 inhibitor and starve the cancer cell of necessary energy resulting in cytotoxic effect, apoptotic effect, or inhibition of replication.

Selectivity to Cancer Cells as a Result of Anaerobic Function of Cancer Cells

The invention, either in the preferred mode of lovastatin and rofecoxib, or the alternative preferred mode of lovastatin, rofecoxib and cystine, takes advantage of the increased ratio of anaerobic to aerobic functionality of a cancer cell compared to that ration in a normal cell. In the process of replication and mitosis, the growth rates of cancers parallel their level of differentiation and the relative number of their cells in mitosis. Mitoses are more abundant in the anaplastic rapidly dividing variants, meaning in the cancer cells that are creating "clones" of each other by cell division and replication. In most cancers that are associated with an increased number of mitoses and growth rate of cells, such proliferative activity results from the apparent loss of regulatory mechanisms apparent in normal cells. Cancer cells, without these regulatory mechanisms, are so engaged in the mitosis process with its significant energy demands, that both aerobic energy generation and anaerobic energy generation mechanisms are utilized. Nelson and Cox, Lehninger, Principles of Biochemistry (3$^{rd}$ ed. 2000) at 541.

In a normal cell, the combination of glutathione and internal cell biochemical controls enable an efficient disposition of cell wastes. In a cancer cell, the anaerobic processes of the cell to meet the cell's energy demands result in use of glycolytic mechanisms even in the presence of what would be adequate oxygen supplies in a normal cell. The increased glycolytic processes, particularly the anaerobic processes, generate relative more waste product such as CO2 and lactic acid. Metabolism at a Glance, J. G. Salway, p. 32–33, 68–69 (Blackwell Science Ltd., Oxford and London, 2$^{nd}$ ed. 1999). Moreover, the COX-2 inhibitor shifts the reaction equilibrium to promote a higher concentration of arachidonic acid. Biochemistry, Geigy Scientific Tables, Book 4, ed. by C. Lemtner, publ. by Ciba-Geigy (1986), p. 25–27; Fosslien, "Biochemistry of Cyclooxygenase (COX)-2 Inhibitors and Molecular Pathology of COX-2 in Neoplasia," Crit. Rev. in Clin. Lab. Sci. 37(5): 431, 433 (November 2000). Such relatively acidic environment in the cancer cell interferes with the functionality of the glutathione pathway which pathway is less efficient in an acidic environment.

Classic biochemistry indicates that the concentration of glutathione will fall in a moe acidic environment such as the relatively more acidic cancer cell. Glutathione is gamma-Glu-Cys-Gly. The COO– ion on the end of the chain will be more present and a more favored species in the less acidic environment of the normal cell.

The glutathione functionality is important in reducing reactive oxygen species to relieve subsequent oxidative stress which is deleterious to any cell. The effect in the cancer cell of the relatively reduced glutathione functionality and generation of increased wastes from increased and unregulated glycolysis is to either cause a slowing of the processes leading to waste production, thereby slowing replication, or to cause a change in osmolarity of the cell which is normally offset by increased water and a corresponding change in cell size. By contrast, in normal cells, an enhancement in relief of oxidative stress occurs, as well as maintenance of full functionality, thereby strengthening the immune system competency and total body system.

Another accomplishment of the invention not suggested by the literature is to utilize cystine to ameliorate the negative renal, hepatic and gastric effects of COX-2 inhibitors and HMG-CoA inhibitors, both as a combination and individually. Unfortunately, like many non-steroidal antiinflammatory (NSAIDs), the COX-2 inhibitors are felt to cause a range of gastrointestinal problems. This amelioration by the invention of negative renal, gastric and hepatic effects is accomplished by cystine, especially in a glutathione deficient patient.

The avoidance of a glutathione deficiency steers the patient to have a higher Th-1 response to Th-2 response ratio than the patient would have with any glutathione deficiency. Peterson, J. et al, "Glutathione levels in antigen-presenting cells modulate Th1 versus Th2 response patterns," Vol 95(6), Proceedings Nat'l Acad. Sci. USA p. 3071–76 (Mar. 17, 1998). This ameliorates negative gastrointestinal hepatic and renal effects. Another article, discussing 5-HETE and its association with prostate cancer, suggests that N-acetyl cysteine in the invention would not be efficacious. Miller et al,, "5-HETE Congeners as Modulators of Cell Proliferation," Bioorg. Med. Chem. Ltr. 10(17): 913–916 (Sep. 4, 2000).

The second and unexpected enhancement is independent of, but corollary to, the combination of the COX-2 inhibitor and HMG-CoA inhibitor. Though no source is cited, Fosslien suggests that antioxidants such as TROLOX also inhibit COX-2 induction: "Inhibitors of COX-2 induction are tumor suppressor protein p53, estrogen, and antioxidants such as Trolox (N-acetylcysteine, 6-hydroxy-2,5,7,8-tetramethylchroman-2-carboxylic acid), PDTC, and U75006" Fosslien, "Biochemistry of Cyclooxygenase (COX)-2 Inhibitors and Molecular Pathology of COX-2 in Neoplasia," Crit. Rev. in Clin. Lab. Sci. 37(5): 431, 433 (November 2000). TROLOX is not practical for combating cancer in mammals because it is an extremely powerful anti-oxidant and potentially toxic. In this invention, a more specific anti-oxidant that affects the glutathione pathway and which will have additional COX-2 inhibition characteristics is used. See Fosslien, Crit. Rev. in Clin. Lab. Sci. 37(5): 431 (November 2000).

The correlative effect is that the invention takes advantage of the very "strengths" of the vigorously metastasizing cancer whose strengths weaken the cancer cell's response to cystine and the glutathione pathway because of the cancer cell's Gompertzian growth characteristic.

Lovastatin, its Interaction with a Selective COX-2 Inhibitor and Isoprostanes and the Lipoxygenase Pathway The cited article entitled, "Caspase-7 is Activated During Lovastatin Induced Apoptosis of the Prostate Cancer Cell Line LNCaP" 58(1) Cancer Research: 76–83 (1998), and a second article, Lee et al, "Inhibition of the 3-hydroxy-3methylglutaryl-coenzyme A reductase pathway Induces p53-independent Transcriptional Regulation of p21 (WAF1/CIP1) in human prostate carcinoma cells", 273(17) J. Biol. Chem.:10628–23, (1998), reported that lovastatin had therapeutic value in treating prostate cancer. Patients to whom were administered lipid lowering/modifying drugs such as lovastatin were suggested to be more cancer-free than those using bile acid-binding resins. See, 3-Hydroxy-3-Methylglutaryl Coenzyme A Reductase Inhibitors and the Risk of Cancer: A Nested Case-Control Study, 160(5) Archives of Internal Med: 2363–2368 (2000).

Lovastatin can be predicted to have another cooperative effect with rofecoxib with respect to cancer, especially prostate cancer. There is strong evidence that oxidative stress and subsequent free radical damage is very important in prostate cancer. Chung et al, Prostate Cancer: Biology, Genetics and the New Therapeutics, "Chemoprevention of Prostate Cancer" by Brooks and Nelson p. 365–375 at p. 369(Humana Press 2001).

COX-2 Inhibitor and the Lipooxygenase Pathway

In examining the cyclooxygenase pathway, see Biochemistry, Geigy Scientific Tables, Book 4, ed. by C. Lemtner, publ by Ciba-Geigy (1986), p. 25, by application of Le Chatelier's principle, an inhibition of the cyclooxygenase pathway will cause the concentration of arachidonic acid to increase. Such increased concentration will cause an increase in products produced in the lipooxygenase pathway. One of those products is Leukotriene B4. Leukotriene B4 is implicated in lipoperoxidative stress to cells.

The Lipooxygenase Pathway and Isoprostanes

As a cancer cell signals for increased COX-2 expression which is being inhibited, the signal is directed to creation of further arachidonic acid ("AA"). The differentiation from normal cells is that a normal cell is not signaling for more AA to delivery more COX-2 expression. From both COX-2 inhibition and saturation from products of AA in the lipooxygenase ("LPO") pathway, a significant buildup of AA occurs which can be most easily relieved from a redox viewpoint by creation of isoprostanes.

Such excess production has implications for the lipooxygenase metabolic pathway. The evidence for this lipooxygenase pathway effect is seen in isoprostanes which are prostaglandin-like compounds which are formed by free radical catalysed peroxidation of arachidonic acid esterified in membrane phospholipids (Neurochem Res October 2000; 25(9–10):1357–64).

Unfortunately for the cancer cell, isoprostanes are indicators of damage to membrane phospolipids. Arachidonic acid (AA) is sterified in the membrane phospholipids, and when oxidized, isoprostanes are the end-product. The peroxidation products are monitored by measuring the isoprostanes and lipid peroxides. For a rapidly dividing cancer cell in which membrane synthesis is critical, the increase in arachidonic acid and its potential damage to membrane phospholipids has negative implications for replication success. The rise in isoprostane levels shows that oxidation of excess arachidonic acid is occurring. This is one mechanism for the damage from excess arachidonic acid that may be seen with the use of the COX-2 inhibitors and contributes to explaining the toxic effect of a COX-2 inhibitor, especially in rapidly dividing cells. However, presence of the isoprostane in the blood or urine would signal an upper limit has been reached of the COX-2 inhibitor above which the risk of kidney or liver damage may increase.

Lipid peroxidation is best characterized as a series of chain breaking reactions in the lipid bi-layer at the membrane which inhibits the proper growth of proteins. The membrane is rendered more porous and susceptible to degeneration, or to penetration by other molecules in the body's immune system. Analogously, lipid peroxidation by heat occurs in an egg white when heated. In the body, and as is desired in cancer cells, such lipid peroxidation occurs chemically.

The HMG-CoA reductase inhibitor simvastatin has been shown to produce positive effects in the endothelial lining of blood vessels even independent of its lipid lowering effects. Animals with high cholesterol diets who exhibited continued high serum cholesterol who were administered simvastatin demonstrated a lower rate of production of F(2)-isoprostanes and thiobarbituric acid-reactive substances (TBARS), markers of oxidative stress, than animals who were not treated with simvastatin and maintained on a high cholesterol diet. Arterioscler Thromb Vasc Biol January 2001; (1):122–8). Simvastatin is an analog of lovastatin, which are both statins produced from *aspergillus terreus*.

The presence of the HMG-CoA reductase inhibitor may contribute to moderating the effects of lipid peroxidation produced in the normal cells moderating production of isoprostanes.

While a protective effective may not seem facially desirable, consideration needs to be made of the selectivity which occurs. The cancer cell metabolic pathways which result in the higher expression of COX-2 in cancer cells, which the invention proposes to inhibit, suggest that cancer cells utilize COX-2 in a meaningful way, a conclusion supported by the apparent partial efficacy of COX-2 inhibitors against cancer. In order to obtain COX-2, cancer cells have a signaling system to stimulate the precursor of COX-2, which is arachidonic acid. Normal cells which do not have a similar need for COX-2 apparently do not have such a signaling system.

For a cancer cell which under normal replication conditions will experience a more rapid genesis of lipid peroxidation products from membrane synthesis, the inventors surmise that the partial protective effect of a statin to slow the rise in isoprostane levels is selectively insufficient to protect the cancer cell from excess arachidonic acid, while acting protectively in normal cells. As a corollary, whatever offsetting benefit the statin may have against the lipooxygenase pathway products is not sufficient to overcome either the toxic effects of excess arachidonic acid, nor to offset the cholesterol synthesis inhibition occurring in the cholesterol synthesis pathway with respect to production of mevalonate and occurring with respect to excess geraniol as a result of interference with squalene conversion to cholesterol.

Thus, there is a selective effect of increased toxic metabolites when a COX-2 inhibitor is administered as evidenced by increased isoprostane levels, with end products that have primary toxicity to cancer cells from excess lipid peroxidation and the LTEB4. Biochemistry, Geigy Scientific Tables, Book 4, ed. by C. Lemtner, publ by Ciba-Geigy (1986), p. 25–27, 142–147.

Testing of isoprostanes and TBAR's can be used to determine if excessive amounts of lovastatin or any statin are being used and as an indicator of the level of lipooxygenase perodixation effects.

Another product that can result from increased arachidonic acid is 5-HETE which has been implicated in prostate cancer. Miller et al, "5-HETE Congeners as Modulators of Cell Proliferation," Bioorg. Med. Chem. Ltr. 10(17): 913–916 (Sep. 4, 2000). It is poorly disposed of. However once saturated, it will cause increased arachidonic acid buildup if arachidonic acid buildup is being artificially stimulated such as by a COX-2 inhibitor. Further evidence of this effect of increased AA concentration is shown from experiments with γ-linoleic acid which is the precursor of arachidonic acid through the formation of dihomo-γ-linoleic acid ("Metabolism at a Glance", Salway, $2^{nd}$ edition, Black-Well Sciences, UK pg. 86). Conjugated linoleic acid (CLA) is prone to oxidation, and it has been suggested that increased oxidation of lipids may contribute to an antitumorigenic effects of this agent. Clin Sci (Colch) December 2000; 99(6):511–6. There, researchers followed levels of 8-iso-prostaglandin F(2alpha) (8-iso-PGF(2alpha)), a major isoprostane, and of 15-oxo-dihydro-PGF(2alpha), a major metabolite of PGF(2alpha), (collectively referred to as isoprostanes) and tested their levels, as indicators of non-enzymic and enzymic arachidonic acid oxidation respectively after dietary supplementation with CLA in middle-aged men (mean age 53 years) with abdominal obesity for 1 month in a randomized controlled trial. Thus, the addition of CLA to the diet of people undergoing metabolic cancer therapy with a Hmg-CoA and a COX-2 inhibitor would result in an enhanced effect by increasing the lipid oxidation effect of the isoprostanes, and shows the creation of excess arachidonic acid has antitumorigenic effect as predicted by the inventors.

Using the isoprostane levels as indicators, the treatment dose of the COX-2 inhibitor can be maximized to give the maximum tolerated dose for use in cancer therapy without creating excessive systemic toxicity. More lipid oxidation activity indicates increased oxidative stress, usually a characteristic of cancer activity. A long-term falling level of isoprostanes will mean for COX-2 expressing cancers that there is relatively less cancer risk. An ELISA test for isoprostane level is available from Cayman Chemical Company, 11800 E. Ellsworth Rd., Ann Arbor, Mich.

For a membrane-impaired cancer cell, receptors and transport molecules for materials needed for cell survival tend to be overloaded and the cell does not function properly, much less have much chance of replicating accurately with an intact membrane. Additionally, in this invention, the shift in concentration caused by excess ubiquinones toward semiquinone triggers increased lipid peroxidation. Nohl, "Antioxidant-derived prooxidant formation from Ubiquinol," Free Radical Biol. Med. 25(6): 666–675 (October 1998). While the statin can ameliorate the tendency to lipid peroxidation, which is why a lower dose is preferred, it need only be sufficient to impair cholesterol synthesis, and there remain sufficient lipid peroxidants to damage cancer cells while normal cells are slightly protected.

The presence of ubiquinones in normal cells with adequate glutathione does not materially change their characteristics; however in cancer cells, the excess ubiquinones in combination with the already nascent tendency to express lipid peroxidation sufficiently the weakens the cells to expose them to immune system attack, a tendency not overcome by the presence of glutathione which is less active in the more anaerobic environment of a cancer cell.

Lovastatin and its Inhibition of Farnesyl Pyrophosphate and Generaylgeranylpyrophosphate Lovastatin has another inhibitory effect which has implications for both cholesterol synthesis, ubiquinone concentration, and farnesyl pryrophosphate concentration. "Lovastatin, an HMG-CoA reductase inhibitor that inhibits the biosynthesis of farnesylpyrophosphate (FPP) and geranylgeranylpyrophosphate (GPP), is used routinely as a positive control for inhibition of processing of both geranylgeranylated and farnesylated proteins [citations omitted]." A. Vogt et al, "A Non-peptide Mimetic of Ras-CAAX: Selective inhibition of Farnesyl Transferase and Ras Processing," 270(2) J. Biol. Chem. 660–664 (2000). In addition to additional direct cholesterol inhibition, Salway, Metabolism at a Glance at 88–89 (Blackwell Science $2^{nd}$ ed. 1999), the effect of any FPP inhibition is to directly inhibit production of dolichols, which has implications for dolichol phosphate which affects messenger RNA transcription. Since cancer cells are attempting to replicate, a selective effect on cancer cells by affecting messenger RNA is achieved. Lehninger on Biochemistry at 1059, $3^{rd}$ ed. GPP inhibition likely has the same effect as post-lanosterol cholesterol cycle inhibition in that additional energy must be used to overcome inhibitory effects. The Vogt article also notes that cysteine is important in ras oncogene activation. This teaches away from the benefits of glutathione pathway protection, but the inventors suggest that the combination of diversion of glutathione pathway resources to stabilize other adversely affected metabolic pathways of a cancer cell is likely sufficient in combination with FPP and GPP inhibition to interfere with cell replication. What FPP is generated will be diverted to enhance cholesterol synthesis making it less available for ras oncogene activation in conjunction with cysteine.

Lipid Peroxidation and Reactive Oxygen and Nitrogen Species

The article entitled "Reactive Oxygen and Nitrogen Species: Efficient, Selective, and Interactive Signals During Intercellular Induction of Apoptosis; Georg Bauer, Abteilung Virologie, Institute for Medizinische Mikrobiologie und Hygiene, Universität Freiburg, D-79104 Freiburg, Germany; *Anticancer Research* 20: 4115–4140 (2000) contains a comprehensive discussion of the interplay of reactive nitrogen species and oxygen species with apoptosis. See also, Bolanos, Nitric Oxide, Mitochondrial Function and Excitotoxicity, Methods Findings Exp. Clin Pharmacol, 2000, 22(6): 375–77. The Bauer article sets out a series of chemical equations related to processing of reactive oxygen and nitrogen species.

The issue is what about a selective COX-2 inhibitor, the overproduction of ubiquinones, and the interference with mitochrondrial respiration, assuming an adequate supply of glutathione, enables the invention to be effective. We have already recognized that additional energy will be needed to generate cholesterol both because of HMGCoA inhibition and squalene-to-cholesterol synthesis inhibition.

The answer from the Bauer article focuses on the tendency of excess NO and OH species, particularly in their free radical forms, to accelerate lipid degeneration.

As stated previously, lipid peroxidation is best characterized as a series of chain breaking reactions in the lipid bi-layer at the membrane which inhibits the proper growth of proteins. The membrane is rendered more porous and susceptible to degeneration, or to penetration by other molecules in the body's immune system.

In an article entitled "Antioxidant-Derived Prooxidant Formation from Ubiquinol . . . ," Nohl et al, Free Radical Biol. Med. 25(6): 666–75 (October 1998) set forth that "Our studies on the antioxidant activity of ubiquinol in peroxidizing lipid membranes demonstrate the existence of ubisemiquinone (SQ•) as the first reaction product of ubiquinol. A reaction of SQ• derived from the localization allows an access of protons and water from the aqueous phase to SQ• [,] a prerequisite earlier found to trigger autoxidation. Superoxide radicals emerging from this fraction of autoxidizing SQ• form $H_2O_2$ by spontaneous dismutation. SQ• not involved in autoxidation may react with $H_2O_2$. Transfer of the odd electron to $H_2O_2$ resulted in HO• and HO— formation by homolytic cleavage. An analogous reaction was also possible with lipid hydroperoxides which accumulate in biological membranes during lipid peroxidation. The reaction products emerging from this reaction were alkoxyl radicals. Both HO• and alkoxyl radicals are strong initiators and promoters of lipid peroxidation." Id. Abstract to "Antioxidant-Derived Prooxidant Formation from Ubiquinol . . . ," Nohl et al, Free Radical Biol. Med. 25(6): 666–75 (October 1998).

To summarize the important postulates of Bauer with respect to their interrelationship with this invention, first, •NO in the presence of O2•— forms perooxynitrite ONNO—. This is not stable. Interestingly, this peroxynitrite is not a free radical. However, in the acidic environment of a cancer cell, there is a propensity to form "the instable peroxynitrous acid . . . Peroxynitrite has the potential for lipid peroxidation (no formula shown [in the article]). Id. at 4119. "Singlet oxygen, formed after interaction of hydrogen peroxide and peroxynitrite [f.n. omitted] has an extremely short half-life and has the potential for lipid peroxidation [f.n. omitted]. Nitric oxide, though being a free radical shows a long range of action and rather low toxicity. It inhibits lipid peroxidation and caspases. Interaction of nitric oxide with superoxide anions causes the formation of peroxynitrite, a potent lipid peroxidant and apoptosis inducer." Id. at 4116. There are a series of reactions, several of which involve glutathione.

The positive empirical results from the patients on which this invention was tested indicate that peroxynitrite acts as a strong oxidant when increased there is cytokine production. With the increase in ubiquinones causing increased production of superoxide, relatively more of which is available in cancer cells to cause peroxynitirite formation at appropriate pH, the peroxynitrite can cause direct damage to proteins. The second and third reactions discussed are degeneration by homolysis, •OH—+•NO2, or heterolysis degenerating to •OH—+NO+. Even the fourth reaction, ONOOH to ONOOH+ is troublesome for a cancer cell because of the creation of a more acidic environment.

Equally apparent from the equations is the importance of glutathione in detoxification of radical species and prooxidant species such as ONNO—. Glutathione is thought to have a protective effect in a number of instances. However, as postulated, glutathione functions more actively in an anaerobic environment. As a cancer cell's energy needs are stressed by a COX-2 inhibitor, more anaerobic respiration occurs, lowering the pH of the cancer cell slightly, shifting even glutathione reactions away from oxidation to more benign species and generating more free radical damage and accelerating lipid peroxidation. While cancer cells having complete angiogenesis will be less affected by these reactions, the inclination to apoptosis and the degeneration of angiogenic species either as a result of the death of a cell, or the waste of energy in the tumor to generate unutilized angiogenesis both inhibit the cancer cell's growth. Bauer notes that his key reactions occur early in tumor development prior to angiogenesis, Bauer, 20 AntiCancer Research at 4115, a result consistent with the inventors' clinical observation that cancer is not eliminated but retarded or managed by the invention.

The presence of ubiquinones in normal cells with adequate glutathione does not materially change their characteristics; however, in cancer cells, the excess uniquinones in combination with the already nascent tendency to express lipid peroxidation sufficiently weakens the cells to expose them to immune system attack, a tendency not overcome by the presence of glutathione which is less active in the more anaerobic and more acidic environment of a cancer cell.

Metal Complex Ions and Glutathione

Another aspect to consider is that $H_2O_2$ has a potential rescuing effect for cells to blunt NO mediated apoptosis at high cell density. A primary generator of $H_2O_2$ is glutathione reactions which in a normal cell environment remove hydroxyl radicals, and nitric oxide radicals. In conjunction with metal ions, particularly copper, zinc and magnesium, in glutathione competent cells, the $H_2O_2$ breaks down into water. As explained by Bauer, cells are in a sense rescued from apoptosis in that situation. In cells not so equipped, which would include a number of cancer cells in a tumor, more hydroxyl radicals are generated, and there is not a rescue from apoptosis. The fact that, as explained by Bauer, $H_2O_2$ is a far-ranging species that can intercept NO species far from a cell membrane may explain for small cell cancers, where intercellular range is less of an issue, the relatively toxicity and tumorogenicity of those cancers where the range of operation is less of a factor in what self-protective mechanisms the body has to battle the cancer. The presence of HOCl cannot be ignored which Bauer believes interacts with $H_2O_2$ to generate non reactive molecules such as oxygen, water, chloride anions and protons. Bauer, 20 Anti-Cancer Research 4115–4140, generally.

Notably, however, Bauer remarks that the speed of reaction is not significant unless reaction number 3 [HOCl +H2O2 to O2+H2O+Cl—+H+] is blocked by SOD which is more likely to occur in the COX-2 inhibitor affected cancer cell because of the shift in electron concentration generating more potential $O_2$-. Bauer, 20 AntiCancer Research 4118–19. As the kinetics for this reaction to occur become more favorable, SOD, which has been stably attached to Mn, Zn or Cu, is detached as the reaction proceeds and the SOD performs its catalytic function. The resultant free radical metal ion generated, in the presence of HOCl, accelerates lipid peroxidation. Bauer, Anticancer Research 20: 4115–4140 (2000) at 4118–19.

Glutathione (GSH), a critical element in immune system function, unquestionably has some positive effects for the cancer cell because it can scavenge free radicals. Yet this is needed in all cells. Glutathione does have a favorable effect on cancer cells through its protection of the disulfide bridges. Protection of disulfide bridges inhibits lipid peroxidation therefore protecting protein structure, particularly tertiary and quaternary structures. "Glutathione probably helps maintain the sulfhydryl groups of proteins in the reduced state and the iron of heme in the ferrous (Fe2+) state, and it serves as a reducing agent for glutaredoxin in deoxyribonucleotide synthesis (see FIGS. 2–37 [in source]). Its redox function is also used to remove toxic peroxides formed in the normal course of growth and metabolism under aerobic conditions: 2GSH +R—O—O—H to GSSG +H2O+R—OH." Lehninger, Principles of Biochemistry ($3^{rd}$ ed. 2000) at 842. As is apparent from the quotation, any effect on glutathione supply, such as failure to remove toxic peroxides, or lack of presence for deoxyribonucleotide synthesis because of competitive consumption to maintain homeostasis in cancer cells has serious implications for cell division and replication, which is the lifeblood and toxicity of cancer.

Glutathione, however, will be slightly less present in the acidic environments of cancer cells. Glutathione is gamma-Glu-Cys-Gly. The COO— ion on the end of the chain will be more present and a more favored species in a less acidic environment. The more acidic environment of anaerobic glycolysis in cancer cells causes a shift to moderately lower relative glutathione concentrations, and consequently less protection from apoptotic free radical reactions.

The implications of metal ion reactions and glutathione, as seen in the Bauer equations, Anticancer Research 20: 4118–19 (2000), are that glutathione absorption in stabilizing free radicals to convert them to $H_2O_2$ has implications in coincidentally affecting the reaction kinetics of superoxide dismutase (SOD) and affecting the metal ion chemical reactions illustrated by Bauer under "M" at Anticancer Research 20: 4118.

This invention does not propose to be prima facie a cancer cure, but rather a prima facie cancer manager. The competitive consumption of energy to overcome cholesterol synthesis, to overcome interference with mitochrondrial respiration, and the competitive consumption of GSH to thwart lipid peroxidation, and to rescue cancer cells from reactive oxygen and nitrogen species either weakens existing cells, weakens newly generated cells (which may then undergo self-apoptosis) or inhibits membrane and DNA synthesis or all of these. The inherent characteristics of replicating cancer cells and the necessary anaerobic enhancement to their energy processes enable the invention to selectively attack cancer cells while normal cells and their homeostatic processes can protect the mammalian organism which the inventors desire to preserve. Moreover, the administration of the compounds in the invention enable the organism to achieve the senescence which cancer cells have attempted to elude through a variety of mechanisms that the body in many instances is helpless to resist. The use of HOCl, and the application of NO•— and OH•— is the usual means to achieve senescence, and the invention enables proper operation of that mechanism.

NADPH Concentration, COX-2 Inhibitors and Apoptosis

A corollary effect of the inhibition of creation of cholesterol relates to the shifting of equilibrium toward to squalene and a higher concentration of NADPH+H+ as a result of the action of the COX-2 inhibitor. As remarked by Bauer, what is at issue is high speed bursts of adjacent $NO/O_2$— activity which can damage membranes and cells. The marginal and momentary increase in NADPH +H+ has a series of contradictory effects. Exterior to the mitochrondria, increased levels of NADPH can be seen to slow reactions in the pentose phosphate pathway, namely in the transition from glucose 6-phosphate to ribulose 5-phosphate. Selective shifts in this pathway affect glucose-6-phosphate, though perhaps only mildly. NADPH concentration shifts also slow the conversion of malate to pyruvate, a precursor to acetyl CoA, a precursor to cholesterol, a possible positive in inhibiting cancer cell membrane synthesis. Another effect is a buildup of lactic acid with concomitant cytotoxic effects for cells unable to tolerate increased acidity. Salway, Id. at pp. 49, 60. Salway remarks on this shift indirectly, noting that "during re-feeding after fasting, glucose is metabolized anaerobically to lactate by muscle even though the conditions are aerobic. This is because, immediately after refeeding, the high ratio of acetyl CoA to pyruvate caused the lingering B-oxidation of fatty acids, results in pyruvate dehydrogenase remaining inhibited. Consequently, glucose in muscle is metabolized to pyruvate which is reduced to lactate. Salway, Metabolism at a Glance (Blackwell Science Oxford 1999) at p. 60. A similar effect occurs occurs for cancer cells affected by an HMG-CoA reductase inhibitor. The increased acetyl CoA buildup in cancer cells causes increased lactate production. Salway, Id. at 51. That lactate tends to slightly acidify the cancer cell, which has implications in induction of apoptosis. In normal cells, homeostasis is such that an Acetyl CoA imbalance is not toxic on refeeding after starvation because the Acetyl CoA/CoA precursor ratio is not affected.

In cancer cells where increased Acetyl CoA has to be present to overcome the inhibition of synthesis of cholesterol, there is a transient increase of acidity, favoring the reaction of peroxynitrite to NO— and OH— apoptotic free radicals.

NADPH is also implicated in the presence of NADPH oxidase in the generation of free electrons leading to O2•— species. As explained by Bauer, these are implicated in induction of apoptosis. In cancer cells demanding cholesterol, as the reactions of intermediates from squalene and lanosterol to cholesterol are slowed by a selective COX-2 inhibitor, there are momentary increases in NADPH. This has apoptotic effects selective to cancer cells as opposed to normal cells.

The discussion above, and the article by Bauer, "Reactive Oxygen and Nitrogen Species: Efficient, Selective, and Interactive Signals During Intercellular Induction of Apoptosis," *Anticancer Research* 20: 4115–4140 (2000), amply confirm and correlate with the observations of Ellerby et al, Measurement of Cellular Oxidation, Reactive Oxygen Species, and Antioxidant Enzymes during Apoptosis, 322 Method in Enzym. 413 (Academic Press 2000), Bortner, Volume Regulation and Ion Transport during Apoptosis, 322

Method in Enzym. 421 (Academic Press 2000) regarding the apoptotic cascade that can be triggered by the osmotic pressures on a cancer cell as it struggles to maintain chemical homeostasis. The chemical kinetics and reactions confirm the clinical observations with respect to the invention. On balance, the tendency of the combinations in the invention is to selectively disfavor cancer cells based on the inventors empirical observations. The inventors also note that the explanation of pharmakinetics is consistent with the tendency of tumors, once expanded to have a mass of necrotic tissue within them (another complicating factor of cancer), suggesting that glutathione activity, accumulation of wastes and apoptosis are natural mechanisms of cancer cells which the science of this invention attempts to exploit at an earlier stage of cancer cell development in order to manage tumor activity.

Metal Complex Interactions

The interaction of nitrous oxide and reactive oxygen species is one of the most important apoptotic triggers in anti-tumor activity. As previously discussed, COX-2 has two interactions with mitochrondrial respiration and ATP utilization, one direct and one indirect. The direct interaction is the lipophilic/hydrophilic orientation which can inhibit the F0/F1 channel in complex IV. Salway, Metabolism at a Glance at 14–15 (Blackwell Science $2^{nd}$ ed. 1999). The indirect interaction is the increased relative production of ubiquinone as a result of the inhibition of cholesterol demethylation.

Metal ions have the capacity to catalyze, in conjunction with superoxide dismutase (SOD), generation of compounds influential in apoptotic process. Bauer, Reactive Oxygen and Nitrogen Species: Efficient, Selective, and Interactive Signals During Intercellular Induction of Apoptosis, *Anticancer Research* 20: 4115–4140 (2000) at 4118. See also, Bolanos, Nitric Oxide, Mitochrondrial Function and Excitotoxicity, Methods Find Exp. Clin. Pharmacol. 2000 22(6): 375–77.

Wink and Mitchell, in Chemical Biology of Nitric Oxide: Insights into Regulatory, Cytotoxic, and Cytoprotective Mechanisms of Nitric Oxide, Free Radical Biol. & Med. 25(4): 434–456, September 1998, suggest that changes in NADPH oxidase and nitric oxide levels can affect the availability of iron in a cell. This has catastrophic implications for a selectively affected cancer cell. Id. at 447.

Selective disturbance of metal ion interaction in cancer cells will enhance any probability of apoptosis engineered by other metabolic mechanisms.

Particular Efficacy for Androgen Responsive Prostate Cancer

The interference with cholesterol synthesis has a further implication for prostate cancer because cholesterol is a precursor to testosterone which has been shown to be an important contributor to prostate cancer. Androgen suppression is a standard therapy for several lines of prostate cancer, but tends to have time limitations before certain cells become androgen insensitive. Prostate Cancer: Biology, Genetics, and the New Therapeutics p. 92 and Ch. 19 at 327–340 (Humana Press, Totowa N.J. 2001). While the body has other offsetting mechanisms to continue to signal for generation of androgen, there is at least a partial biochemical effect resulting from interference with cholesterol synthesis.

The invention is not meant to be limited to the disclosures, including best mode of invention herein, and contemplates all equivalents to the invention and similar embodiments to the invention for humans and mammals and veterinary science. Equivalents include all pharmacologically active racemic mixtures, diastereomers and enantiomers of the listed compounds and their pharmacologically acceptable salts.

We claim:

1. A method of treating at least one cell line of cancer in a mammalian patient, said at least one cancer cell line being sensitive to at least lovastatin and rofecoxib, comprising the following steps;
    combining in a pharmaceutically acceptable carrier a therapeutically effective amount of rofecoxib within the therapeutic window for rofecoxib and a therapeutically effective amount of lovastatin within the therapeutic window for lovastatin to initially achieve a therapeutically effective change in cholesterol, and administering said rofecoxib and lovastatin to said mammalian patient to achieve a therapeutically effective change in progression of said at least one cancer cell line.

2. The method according to claim 1, further comprising the step:
    incorporating in said carrier an excipient to augment immune function, said excipient being characterized by an ability to be a glutathione pathway enhancing and detoxifying compound.

3. The method according to claim 2, wherein said excipient is cystine.

4. A method of treatment of at least one cell line of cancer in a mammalian patient said at least one cancer cell line being sensitive to at least lovastatin and rofecoxib, comprising the following steps:
    administering a dose of lovastatin beginning at 10 mg in daily amount in a pharmaceutically acceptable carrier;
    administering a dose rofecoxib beginning at 12.5 mg in daily amount in a pharmaceutically acceptable carrier,
    adjusting said dose of lovastatin upward after six weeks within the therapeutic window of lovastatin until LDL cholesterol has been lowered at least 10%;
    adjusting said dose of rofecoxib upward each six weeks within the therapeutic window for rofecoxib until at least two inflammatory response markers, tested each six weeks, show therapeutic change: said at least two inflammatory response markers including upregulation of IL-12 and downregulation of IL-10; and
    thereafter, until regression of tumor or a decrease in tumor progression, adjusting both doses upward on a six-week basis by at least 10% of the previous dose being given within the therapeutic window for each of rofecoxib and lovastatin.

5. The method according to claim 4, further comprising:
    combining a therapeutically effective amount of a glutathione pathway enhancing and detoxifying compound with said rofecoxib and lovastatin to achieve a therapeutically effective change in progression of cancer.

6. The method according to claim 5, wherein said glutathione pathway and detoxifying compound is cystine.

7. A method of treating at least one cell line of cancer in a mammalian patient, said at least one cancer cell line being sensitive to at least lovastatin and rofecoxib, comprising the following steps:
    combining in a pharmaceutically acceptable carrier a therapeutically effective amount of rofecoxib within the therapeutic window for rofecoxib, and a therapeutically effective amount of lovastatin within the therapeutic window for lovastatin to initially achieve a therapeutically effective change in cholesterol, and a therapeutically effective amount of a glutathione pathway enhancing and detoxifying compound with said rofecoxib and lovastatin to achieve a therapeutically effective change in progression of cancer.

8. The method according to claim 7, wherein said glutathione pathway and detoxifying compound is cystine.

9. A method of treatment of at least one cell line of cancer in a mammalian patient, said at least one cancer cell line being sensitive to at least lovastatin and rofecoxib, comprising the following steps:

administering a dose of lovastatin beginning at 10 mg in a daily amount in a pharmaceutically acceptable carrier;

administering a dose rofecoxib beginning at 12.5 mg in a daily amount in a pharmaceutically acceptable carrier, adjusting said dose of lovastatin upward after six weeks within the therapeutic window of lovastatin until LDL cholesterol has been lowered at least 10%;

adjusting said dose of rofecoxib upward each six weeks until therapeutically effective upregulation of isoprostane and lipid peroxidation; and thereafter, until regression of tumor or a decrease in tumor progression, adjusting both doses upward on a six-week basis by at least 10% of the previous dose being given within the therapeutic window for each of rofecoxib and lovastatin.

10. The method according to claim 9, further comprising:

combining a therapeutically effective amount of a glutathione pathway enhancing and detoxifying compound with said rofecoxib and lovastatin to achieve a therapeutically effective change in progression of cancer.

11. The method according to claim 10, wherein said glutathione pathway and detoxifying compound is cystine.

* * * * *